(12) United States Patent
Wentorf et al.

(10) Patent No.: US 8,613,775 B2
(45) Date of Patent: Dec. 24, 2013

(54) ASYMMETRIC TIBIAL COMPONENTS FOR A KNEE PROSTHESIS

(75) Inventors: Mary S. S. Wentorf, Warsaw, IN (US);
Jeffrey E. Bischoff, Warsaw, IN (US);
Raymond C. Parisi, Wakarusa, IN (US);
Katherine M. Rettig, Cincinnati, OH (US)

(73) Assignee: Zimmer, Inc., Warsaw, IN (US)

( * ) Notice: Subject to any disclaimer, the term of this patent is extended or adjusted under 35 U.S.C. 154(b) by 105 days.

(21) Appl. No.: 13/189,336

(22) Filed: Jul. 22, 2011

(65) Prior Publication Data

US 2012/0022659 A1 Jan. 26, 2012

Related U.S. Application Data

(60) Provisional application No. 61/381,800, filed on Sep. 10, 2010, provisional application No. 61/367,375, filed on Jul. 24, 2010.

(51) Int. Cl.
*A61F 2/38* (2006.01)

(52) U.S. Cl.
USPC .................................... 623/20.32; 623/20.28

(58) Field of Classification Search
USPC .......... 623/20.21, 20.28, 20.29, 20.31, 20.32, 623/20.33
See application file for complete search history.

(56) References Cited

U.S. PATENT DOCUMENTS

| | | | |
|---|---|---|---|
| 4,714,474 A | 12/1987 | Brooks, Jr. et al. |
| 4,769,040 A | 9/1988 | Wevers |
| 4,936,853 A | 6/1990 | Fabian et al. |
| 4,950,298 A | 8/1990 | Gustilo et al. |
| 4,959,071 A | 9/1990 | Brown et al. |
| 4,963,152 A | 10/1990 | Hofmann et al. |
| 5,047,058 A | 9/1991 | Roberts et al. |
| 5,061,271 A | 10/1991 | Van Zile |
| 5,071,438 A | 12/1991 | Jones et al. |
| 5,133,758 A | 7/1992 | Hollister |
| 5,137,536 A | 8/1992 | Koshino |
| 5,192,328 A | 3/1993 | Winters |

(Continued)

FOREIGN PATENT DOCUMENTS

| | | |
|---|---|---|
| CN | 103118634 A | 5/2013 |
| CN | 103118635 A | 5/2013 |

(Continued)

OTHER PUBLICATIONS

Design Rationale, Smith & Nephew Journal, Bi-Cruciate Stabilized Knee System, Smith & Nephew 2006.

(Continued)

*Primary Examiner* — David H Willse
*Assistant Examiner* — Javier Blanco
(74) *Attorney, Agent, or Firm* — Schwegman, Lundberg & Woessner P.A.

(57) ABSTRACT

An orthopaedic tibial prosthesis includes a tibial baseplate with an asymmetric periphery which promotes proper positioning and orientation on a resected tibia, while also facilitating enhanced kinematics, soft-tissue interaction, and long-term fixation of the complete knee prosthesis. The asymmetric baseplate periphery is sized and shaped to substantially match portions of the periphery of a typical resected proximal tibial surface, such that proper location and orientation is evident by resting the baseplate on the tibia. The baseplate periphery provides strategically positioned relief and/or clearance between the baseplate periphery and bone periphery, such as in the posterior-medial portion to prevent deep-flexion component impingement, and in the anterior-lateral portion to avoid undue interaction between the anatomic iliotibial band and prosthesis components.

58 Claims, 12 Drawing Sheets

(56) References Cited

U.S. PATENT DOCUMENTS

| | | |
|---|---|---|
| 5,246,459 A | 9/1993 | Elias |
| 5,271,737 A | 12/1993 | Baldwin et al. |
| 5,282,861 A | 2/1994 | Kaplan |
| 5,282,868 A | 2/1994 | Bahler |
| 5,282,870 A | 2/1994 | Moser et al. |
| 5,290,313 A | 3/1994 | Heldreth |
| 5,326,361 A | 7/1994 | Hollister |
| 5,344,460 A | 9/1994 | Turanyi et al. |
| 5,405,396 A | 4/1995 | Heldreth et al. |
| 5,413,604 A | 5/1995 | Hodge |
| 5,413,605 A | 5/1995 | Ashby et al. |
| 5,507,820 A | 4/1996 | Pappas |
| 5,556,433 A | 9/1996 | Gabriel et al. |
| 5,609,639 A | 3/1997 | Walker |
| 5,609,641 A | 3/1997 | Johnson et al. |
| 5,609,645 A | 3/1997 | Vinciguerra |
| 5,613,970 A | 3/1997 | Houston et al. |
| 5,755,802 A | 5/1998 | Gerber |
| 5,824,102 A | 10/1998 | Buscayret |
| 5,871,539 A | 2/1999 | Pappas |
| 5,879,394 A | 3/1999 | Ashby et al. |
| 5,928,286 A | 7/1999 | Ashby et al. |
| 5,964,808 A | 10/1999 | Blaha et al. |
| 6,004,351 A | 12/1999 | Tomita et al. |
| 6,013,103 A | 1/2000 | Kaufman et al. |
| 6,039,764 A | 3/2000 | Pottenger et al. |
| 6,068,658 A | 5/2000 | Insall et al. |
| 6,074,425 A | 6/2000 | Pappas |
| 6,090,144 A | 7/2000 | Letot et al. |
| 6,102,954 A | 8/2000 | Albrektsson et al. |
| 6,102,955 A | 8/2000 | Mendes et al. |
| 6,197,064 B1 | 3/2001 | Haines et al. |
| 6,203,576 B1 | 3/2001 | Afriat et al. |
| RE37,277 E | 7/2001 | Baldwin et al. |
| 6,258,127 B1 | 7/2001 | Schmotzer |
| 6,379,388 B1 | 4/2002 | Ensign et al. |
| 6,413,279 B1 | 7/2002 | Metzger et al. |
| 6,506,216 B1 | 1/2003 | McCue et al. |
| 6,709,461 B2 | 3/2004 | O'neil et al. |
| 6,770,078 B2 | 8/2004 | Bonutti |
| 6,869,448 B2 | 3/2005 | Tuke |
| 6,923,832 B1 | 8/2005 | Sharkey et al. |
| 6,953,479 B2 | 10/2005 | Carson et al. |
| 7,025,788 B2 | 4/2006 | Metzger et al. |
| 7,083,652 B2 | 8/2006 | McCue et al. |
| 7,153,326 B1 | 12/2006 | Metzger |
| 7,189,262 B2 | 3/2007 | Hayes, Jr. et al. |
| 7,264,635 B2 | 9/2007 | Suguro et al. |
| 7,294,149 B2 | 11/2007 | Hozack et al. |
| 7,309,362 B2 | 12/2007 | Yasuda et al. |
| 7,445,639 B2 | 11/2008 | Metzger et al. |
| 7,497,874 B1 | 3/2009 | Metzger et al. |
| 7,513,912 B2 | 4/2009 | Hayes, Jr. et al. |
| 7,544,211 B2 | 6/2009 | Rochetin |
| 7,585,328 B2 | 9/2009 | Haas |
| 7,625,407 B2 | 12/2009 | Akizuki et al. |
| 7,628,818 B2 | 12/2009 | Hazebrouck et al. |
| 7,635,390 B1 | 12/2009 | Bonutti |
| 7,695,519 B2 | 4/2010 | Collazo |
| 7,850,698 B2 | 12/2010 | Straszheim-Morley et al. |
| 2002/0072802 A1 | 6/2002 | O'Neil et al. |
| 2002/0120340 A1 | 8/2002 | Metzger et al. |
| 2004/0034432 A1 | 2/2004 | Hughes et al. |
| 2004/0153066 A1 | 8/2004 | Coon et al. |
| 2004/0162620 A1 | 8/2004 | Wyss |
| 2004/0186582 A1 | 9/2004 | Yasuda et al. |
| 2005/0096747 A1 | 5/2005 | Tuttle et al. |
| 2005/0143832 A1 | 6/2005 | Carson |
| 2005/0209702 A1 | 9/2005 | Todd et al. |
| 2005/0267584 A1 | 12/2005 | Burdulis, Jr. et al. |
| 2006/0030945 A1 | 2/2006 | Wright |
| 2006/0142869 A1 | 6/2006 | Gross |
| 2006/0161259 A1 | 7/2006 | Cheng et al. |
| 2006/0195195 A1 | 8/2006 | Burstein et al. |
| 2006/0224244 A1 | 10/2006 | Thomas et al. |
| 2007/0010890 A1 | 1/2007 | Collazo |
| 2007/0135926 A1 | 6/2007 | Walker |
| 2007/0198022 A1 | 8/2007 | Lang et al. |
| 2007/0233269 A1 | 10/2007 | Steines et al. |
| 2008/0021566 A1 | 1/2008 | Peters et al. |
| 2008/0051908 A1 | 2/2008 | Angibaud et al. |
| 2008/0091271 A1 | 4/2008 | Bonitati et al. |
| 2008/0091272 A1 | 4/2008 | Aram et al. |
| 2008/0091273 A1 | 4/2008 | Hazebrouck |
| 2008/0114462 A1 | 5/2008 | Guidera et al. |
| 2008/0167722 A1 | 7/2008 | Metzger et al. |
| 2008/0215156 A1 | 9/2008 | Duggal et al. |
| 2008/0243258 A1 | 10/2008 | Sancheti |
| 2008/0281426 A1 | 11/2008 | Fitz et al. |
| 2008/0288080 A1 | 11/2008 | Sancheti |
| 2009/0036992 A1 | 2/2009 | Tsakonas |
| 2009/0082873 A1 | 3/2009 | Hazebrouck et al. |
| 2009/0088862 A1 | 4/2009 | Thomas et al. |
| 2009/0125114 A1 | 5/2009 | May et al. |
| 2009/0149963 A1 | 6/2009 | Sekel |
| 2009/0149964 A1 | 6/2009 | May et al. |
| 2009/0204222 A1 | 8/2009 | Burstein et al. |
| 2009/0222103 A1 | 9/2009 | Fitz et al. |
| 2009/0306786 A1 | 12/2009 | Samuelson |
| 2009/0319047 A1 | 12/2009 | Walker |
| 2010/0016978 A1 | 1/2010 | Williams et al. |
| 2010/0016979 A1 | 1/2010 | Wyss et al. |
| 2010/0063594 A1 | 3/2010 | Hazebrouck et al. |
| 2010/0100189 A1 | 4/2010 | Metzger |
| 2010/0125339 A1 | 5/2010 | Earl et al. |
| 2010/0152858 A1 | 6/2010 | Lu et al. |
| 2010/0222890 A1 | 9/2010 | Barnett et al. |
| 2010/0305708 A1 | 12/2010 | Lang |
| 2010/0329530 A1 | 12/2010 | Lang et al. |
| 2011/0082559 A1 | 4/2011 | Hartdegen et al. |
| 2011/0144760 A1 | 6/2011 | Wong et al. |
| 2012/0022658 A1 | 1/2012 | Wentorf |
| 2012/0022659 A1 | 1/2012 | Wentorf |
| 2012/0022660 A1 | 1/2012 | Wentorf |
| 2012/0035735 A1 | 2/2012 | Sanford et al. |
| 2012/0035737 A1 | 2/2012 | Sanford |
| 2012/0101585 A1 | 4/2012 | Parisi et al. |
| 2013/0024001 A1 | 1/2013 | Wentorf et al. |
| 2013/0131820 A1 | 5/2013 | Wentorf et al. |

FOREIGN PATENT DOCUMENTS

| | | |
|---|---|---|
| CN | 103118636 A | 5/2013 |
| EP | 0306744 B1 | 4/1992 |
| EP | 0672397 A1 | 9/1995 |
| EP | 0552950 B1 | 9/1996 |
| EP | 0536457 B1 | 1/1997 |
| EP | 0642328 B1 | 12/1998 |
| EP | 0956836 B1 | 11/1999 |
| EP | 0709074 B1 | 12/2002 |
| EP | 1327424 A1 | 7/2003 |
| EP | 956836 B1 | 7/2004 |
| EP | 1396240 B1 | 4/2008 |
| EP | 1996122 A1 | 12/2008 |
| EP | 0927009 B1 | 1/2009 |
| EP | 1555962 B1 | 2/2011 |
| EP | 2319460 A1 | 5/2011 |
| EP | 2324799 A2 | 5/2011 |
| EP | 2335654 A1 | 6/2011 |
| EP | 2347733 A1 | 7/2011 |
| EP | 0689808 B1 | 9/2012 |
| FR | 2788964 A1 | 8/2000 |
| GB | 2253147 A | 9/1992 |
| GB | 2345446 A | 7/2000 |
| WO | WO94/09725 A1 | 5/1994 |
| WO | WO95/30389 A1 | 11/1995 |
| WO | WO95/35074 A1 | 12/1995 |
| WO | WO-9934755 A1 | 7/1999 |
| WO | WO-0141680 A1 | 6/2001 |
| WO | WO-2005037147 A1 | 4/2005 |
| WO | WO-2005051240 A1 | 6/2005 |
| WO | WO-2006058057 A2 | 6/2006 |
| WO | WO-2007108804 A1 | 9/2007 |
| WO | WO-2007109641 A2 | 9/2007 |

(56) References Cited

FOREIGN PATENT DOCUMENTS

| WO | WO2009/029631 A1 | 3/2009 |
|---|---|---|
| WO | WO-2009088238 A2 | 7/2009 |
| WO | WO2010/008803 A2 | 1/2010 |
| WO | WO-2011072235 A2 | 6/2011 |
| WO | WO2012/018563 A1 | 2/2012 |
| WO | WO2012/018564 A1 | 2/2012 |
| WO | WO2012/018565 A1 | 2/2012 |
| WO | WO2012/018566 A1 | 2/2012 |
| WO | WO2012/018567 A1 | 2/2012 |
| WO | WO-2012112698 A2 | 8/2012 |
| WO | WO-2013077919 A1 | 5/2013 |

OTHER PUBLICATIONS

Tibial Insertion of the Posterior Cruciate Ligament: A Sagittal Plane Analysis Using Gross, Histologic, and Radiographic Methods, Claude Moorman III et al., Arthroscopy: The Journal of Arthroscopic and Related Surgery, vol. 24, No. 3, Mar. 2008, pp. 269-275.
The Attachments of the Fiber Bundles of the Posterior Cruciate Ligament: An Anatomic Study, Andrew Edwards et al., Arthroscopy: The Journal of Arthroscopic and Related Surgery, vol. 23, No. 7, Mar. 2007, pp. 284-290.
Radiological evaluation of the anterolateral and posteromedial bundle insertion sites of the posterior cruciate ligament, Stephan Lorenz et al., Knee Surg Sports Traumatol Arthosc (2009) 17, pp. 683-690.
Product Brochure—Zimmer Gender Solutions Natural-Knee Flex System, Zimmer, Inc. 2007, 2009.
CR Flex, Zimmer NexGen Complete Knee Solution, Surgical Technique for the CR-Flex Fixed Bearing Knee, Zimmer, Inc. 2003.
Zimmer NexGen Complete Knee Solution Extramedullary/ Intramedullary Tibial Resector Surgical Technique, Zimmer, Inc. 2000, 2008, 2009.
Zimmer LPS-Flex Fixed Bearing Knee Surgical Technique, Zimmer 2004, 2007, 2008.
U.S. Appl. No. 13/189,324, Final Office Action mailed Jul. 16, 2013, 19 pgs.
U.S. Appl. No. 13/189,324, Non Final Office Action mailed Dec. 11, 2012, 19 pgs.
U.S. Appl. No. 13/189,324, Response filed Jun. 10, 2013 to Non Final Office Action mailed Dec. 11, 2012, 24 pgs.
U.S. Appl. No. 13/189,328, Non Final Office Action mailed Mar. 19, 2013, 10 pgs.
U.S. Appl. No. 13/189,328, Response filed Jan. 10, 2013 to Restriction Requirement mailed Dec. 10, 2012, 9 pgs.
U.S. Appl. No. 13/189,328, Response filed Jul. 18, 2013 to Non Final Office Action mailed Mar. 19, 2013, 16 pgs.
U.S. Appl. No. 13/189,328, Restriction Requirement mailed Dec. 10, 2012, 6 pgs.
U.S. Appl. No. 13/189,338, Response filed Apr. 15, 2013 to Restriction Requirement mailed Feb. 14, 2013, 18 pgs.
U.S. Appl. No. 13/189,338, Response filed Jul. 17, 2013 to Restriction Requirement mailed Jun. 17, 2013, 16 pgs.
U.S. Appl. No. 13/189,338, Restriction Requirement mailed Feb. 14, 2013, 5 pgs.
U.S. Appl. No. 13/189,338, Restriction Requirement mailed Jun. 17, 2013, 6 pgs.
U.S. Appl. No. 13/189,339, Response filed Apr. 15, 2013 to Restriction Requirement mailed Mar. 6, 2013, 11 pgs.
U.S. Appl. No. 13/189,339, Response filed Jul. 17, 2013 to Restriction Requirement mailed Jun. 17, 2013, 10 pgs.
U.S. Appl. No. 13/189,339, Restriction Requirement mailed Mar. 6, 2013, 6 pgs.
U.S. Appl. No. 13/189,339, Restriction Requirement mailed Jun. 17, 2013, 7 pgs.
U.S. Appl. No. 13/229,103, Response filed Jul. 1, 2013 to Non Final Office Action mailed Apr. 1, 2013, 19 pgs.
U.S. Appl. No. 13/229,103, Non Final Office Action mailed Apr. 1, 2013, 18 pgs.
U.S. Appl. No. 13/593,339, Preliminary Amendment filed Aug. 23, 2012, 6 pgs.
U.S. Appl. No. 13/594,543, Preliminary Amendment filed Aug. 24, 2012, 4 pgs.
Extramedullary/Intramedullary Tibial Resector: Surgical Technique, Nexgen Complete Knee Solution, Zimmer, Inc., (2000, 2008, 2009), 28 pgs.
International Application Serial No. PCT/US2011/045077, International Preliminary Report on Patentability mailed Jul. 5, 2012, 23 pgs.
International Application Serial No. PCT/US2011/045077, International Search Report and Written Opinion mailed Jan. 9, 2012, 15 pgs.
International Application Serial No. PCT/US2011/045078, International Preliminary Report on Patentability mailed Feb. 7, 2013, 11 pgs.
International Application Serial No. PCT/US2011/045078, International Search Report and Written Opinion mailed Jan. 9, 2012, 14 pgs.
International Application Serial No. PCT/US2011/045080, International Preliminary Report on Patentability mailed Feb. 7, 2013, 13 pgs.
International Application Serial No. PCT/US2011/045082, International Preliminary Report on Patentability mailed Feb. 7, 2013, 11 pgs.
International Application Serial No. PCT/US2011/045082, International Search Report mailed Jan. 9, 2012, 5 pgs.
International Application Serial No. PCT/US2011/045082, Written Opinion mailed Jan. 9, 2012, 10 pgs.
International Application Serial No. PCT/US2011/045083, International Preliminary Report on Patentability mailed Feb. 7, 2013, 8 pgs.
International Application Serial No. PCT/US2011/045083, International Search Report mailed Dec. 7, 2011, 2 pgs.
International Application Serial No. PCT/US2011/045083, Written Opinion mailed Dec. 7, 2011, 6 pgs.
International Application Serial No. PCT/US2011/051021, International Preliminary Report on Patentability mailed Mar. 21, 2013, 8 pgs.
International Application Serial No. PCT/US2011/051021, International Search Report mailed Nov. 23, 2011, 12 pgs.
International Application Serial No. PCT/US2011/051021, Written Opinion mailed Nov. 23, 2011, 7 pgs.
International Application Serial No. PCT/US2012/052132, International Search Report mailed Jan. 10, 2013, 5 pgs.
International Application Serial No. PCT/US2012/052132, Invitation to Pay Additional Fees and Partial Search Report mailed Nov. 15, 2012, 7 pgs.
International Application Serial No. PCT/US2012/052132, Written Opinion mailed Jan. 10, 2013, 10 pgs.
International Application Serial No. PCT/US2012/052340, Search Report mailed Oct. 12, 2012, 4 pgs.
International Application Serial No. PCT/US2012/052340, Written Opinion mailed Oct. 12, 2012, 6 pgs.
"NexGen Trabecular Metal Modular Plates", Zimmer Inc., (2007), 19 pgs.
"Tibial Baseplate: Pocket Guide (United States Version)", Zimmer, Inc. (2009), 17 pgs.
"Trabecular Metal Monoblock Tibial Components", Zimmer, Inc., (2007), 4 pgs.
"Trabecular Metal Monoblock Tibial Components Surgical Technique Addendum", Nexgen Zimmer, Inc., (2005, 2007), 12.
"Trabecular Metal Tibial Tray: Surgical Technique", NexGen Zimmer, Inc., (2007, 2009), 16 pgs.
Annayappa, Ramesh, et al., "Tibial Prosthesis", U.S. Appl. No. 13/189,324, filed Jul. 22, 2011, 50 pgs.
Ding, M., et al., "Age-related variations in the microstructure of human tibial cancellous bone", Journal of Orthopaedic Research, 20(3), (2002), 615-621.
Ding, M., et al., "Changes in the three-dimensional microstructure of human tibial cancellous bone in early osteoarthritis", Journal of Bone & Joint Surgery (British), 85-B(6), (Aug. 2003), 906-912.

(56) References Cited

OTHER PUBLICATIONS

Doyle, et al., "Comparative Analysis of Human Trabecular Bone and Polyurethane Foam", Purdue University., 1 pg.

Dunbar, M. J., et al., "Fixation of a Trabecular Metal Knee Arthroplasty Component: A Prospective Randomized Study", The Journal of Bone & Joint Surgery (American), vol. 91-A(7), (Jul. 2009), 1578-1586.

Hvid, Ivan, et al., "Trabecular bone Strength Patterns at the Proximal Tibial Epiphysis", Journal of Orthopaedic Research, vol. 3, No. 4, (1985), 464-472.

Klostermann, et al., "Distribution of bone mineral density with age and gender in the proximal tibia", Clinical Biomechanics 19, 376-376.

Stilling, et al., "Superior fixation of pegged trabecular metal over screw-fixed pegged porous titanium fiber mesh", Acta Orthopaedica., (2011), 177-186.

Wentorf, Mary S. S, "Asymmetric Tibial Components for a Knee Prosthesis", U.S. Appl. No. 13/189,336, filed Jul. 22, 2011, 60 pgs.

International Search Report and Written Opinion mailed Jan. 9, 2012 in related International Application No. PCT/US2011/045080.

International Search Report and Written Opinion mailed Jan. 9, 2012 in related International Application No. PCT/US2011/045082.

U.S. Appl. No. 13/189,338, filed Jul. 22, 2011 in the U.S. Patent Office entitled "Asymmetric Tibial Components for a Knee Prosthesis" and which claims priority to U.S. Appl. No. 61/381,800, from which the present application also claims priority.

U.S. Appl. No. 13/189,339, filed Jul. 22, 2011 in the U.S. Patent Office entitled "Asymmetric Tibial Components for a Knee Prosthesis" and which claims priority to U.S. Appl. No. 61/381,800, from which the present application also claims priority.

U.S. Appl. No. 13/229,103, filed Sep. 9, 2011 in the U.S. Patent Office entitled "Motion Facilitating Tibial Components for a Knee Prosthesis" and which claims priority to U.S. Appl. No. 61/381,800, from which the present application also claims priority.

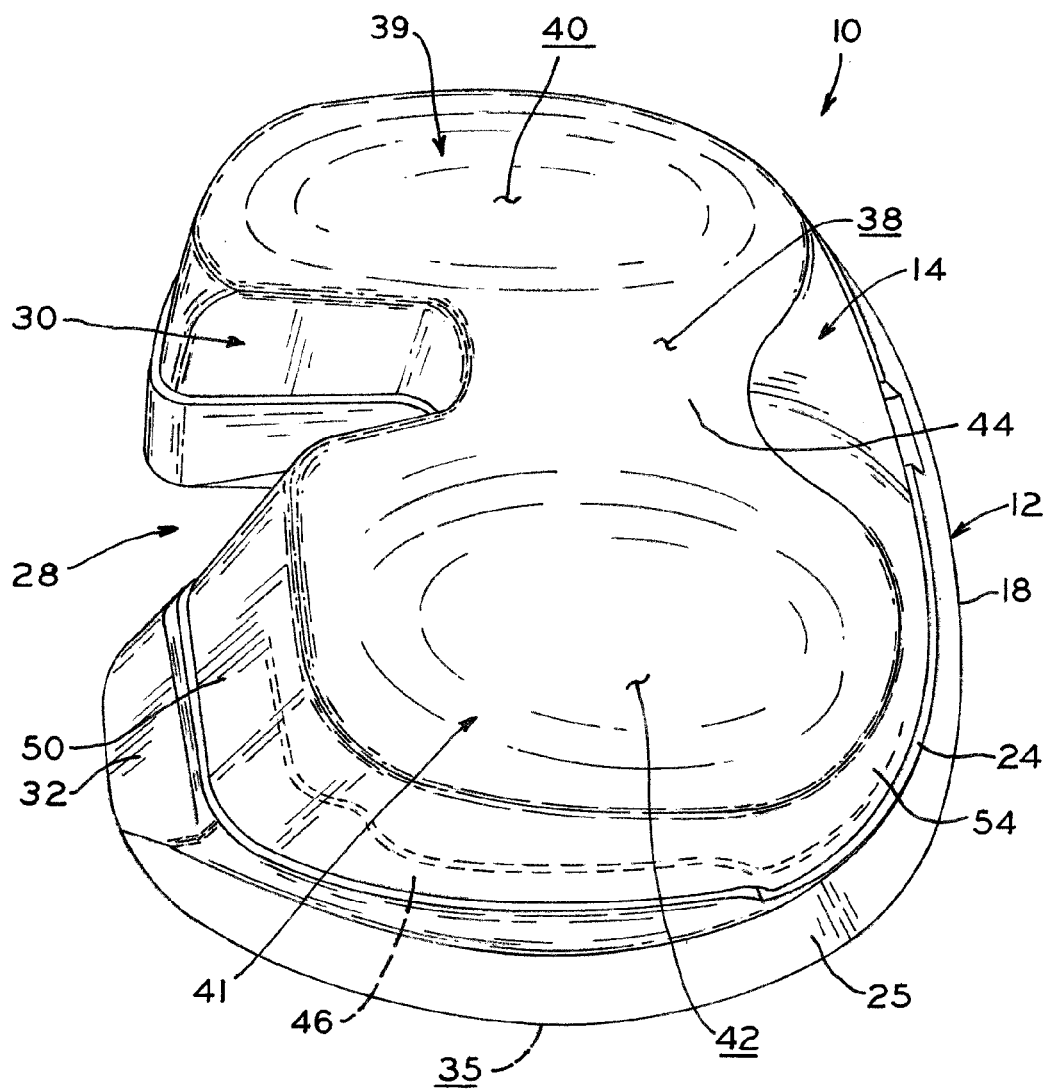
FIG_1B

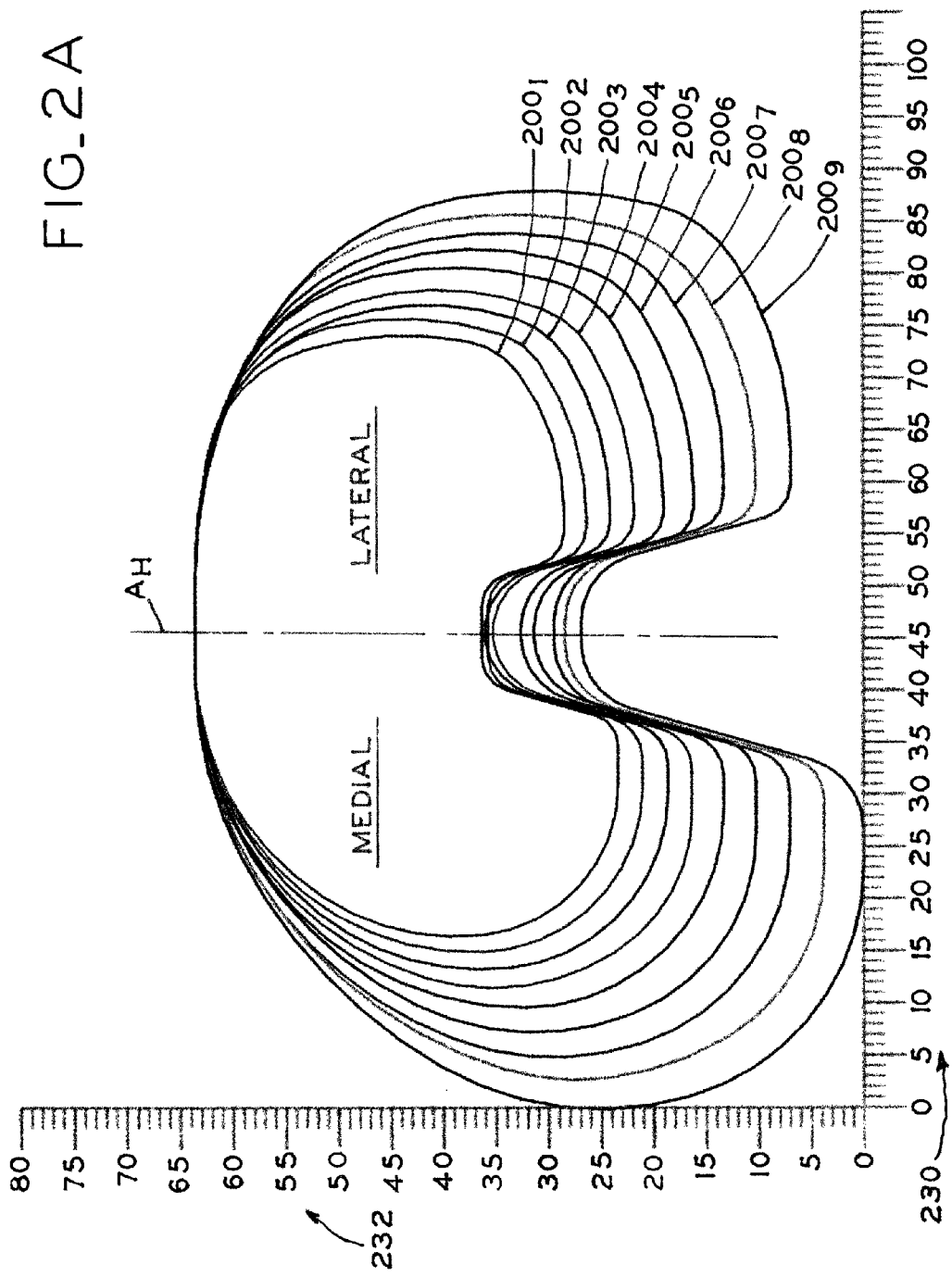

ASYMMETRIC TIBIAL COMPONENTS FOR A KNEE PROSTHESIS

CROSS-REFERENCE TO RELATED APPLICATIONS

This application claims the benefit under Title 35, U.S.C. §119(e) of U.S. Provisional Patent Application Ser. No. 61/381,800, filed on Sep. 10, 2010 and entitled TIBIAL PROSTHESIS FACILITATING ROTATIONAL ALIGNMENT, and U.S. Provisional Patent Application Ser. No. 61/367,375, filed on Jul. 24, 2010 and entitled TIBIAL PROSTHESIS, the entire disclosures of which are hereby expressly incorporated by reference herein.

BACKGROUND

1. Technical Field

The present disclosure relates to orthopaedic prostheses and, specifically, to tibial components in a knee prosthesis.

2. Description of the Related Art

Orthopaedic prostheses are commonly utilized to repair and/or replace damaged bone and tissue in the human body. For example, a knee prosthesis may include a tibial baseplate that is affixed to a resected or natural proximal tibia, a femoral component attached to a resected or natural distal femur, and a tibial bearing component coupled with the tibial baseplate and disposed between the tibial baseplate and femoral component. Knee prostheses frequently seek to provide articulation similar to a natural, anatomical articulation of a knee joint, including providing a wide range of flexion.

The tibial insert component, sometimes also referred to as a tibial bearing or meniscal component, is used to provide an appropriate level of friction and contact area at the interface between the femoral component and the tibial bearing component. For a knee prosthesis to provide a sufficient range of flexion with a desirable kinematic motion profile, the tibial bearing component and tibial baseplate must be sized and oriented to interact appropriately with the femoral component of the knee prosthesis throughout the flexion range. Substantial design efforts have been focused on providing a range of prosthesis component sizes and shapes to accommodate the natural variability in bone sizes and shapes in patients with orthopaedic prostheses, while preserving flexion range and desired kinematic motion profile.

In addition to facilitating implantation and providing enhanced kinematics through manipulation of the size and/or geometry of prosthesis components, protection and/or preservation of soft tissues in the natural knee joint is also desirable.

A given prosthetic component design (i.e., a tibial baseplate, tibial bearing component, or femoral component) may be provided to a surgeon as a kit including a variety of different sizes, so that the surgeon may choose an appropriate size intraoperatively and/or on the basis of pre-surgery planning. An individual component may be selected from the kit based upon the surgeon's assessment of fit and kinematics, i.e., how closely the component matches the natural contours of a patient's bone and how smoothly the assembled knee joint prosthesis functions in conjunction with adjacent soft tissues and other anatomical structures. Soft tissue considerations include proper ligament tension and minimization of soft tissue impingement upon prosthetic surfaces, for example.

In addition to prosthetic sizing, the orientation of a prosthetic component on a resected or natural surface of a bone also impacts surgical outcomes. For example, the rotational orientation of a tibial baseplate and tibial bearing component with respect to a resected proximal tibia will affect the interaction between the corresponding femoral prosthesis and the tibial bearing component. The nature and amount of the coverage of a tibial baseplate over specific areas of the resected proximal tibia will also affect the fixation of the implant to the bone. Thus, substantial design efforts have been focused on providing prosthetic components which are appropriately sized for a variety of patient bone sizes and are adapted to be implanted in a particular, proper orientation to achieve desired prosthesis performance characteristics.

SUMMARY

The present disclosure provides an orthopaedic tibial prosthesis including a tibial baseplate with an asymmetric periphery which promotes proper positioning and orientation on a resected tibia, while also facilitating enhanced kinematics, soft-tissue interaction, and long-term fixation of the complete knee prosthesis. The asymmetric baseplate periphery is sized and shaped to substantially match portions of the periphery of a typical resected proximal tibial surface, such that proper location and orientation is evident by resting the baseplate on the tibia. The baseplate periphery provides strategically positioned relief and/or clearance between the baseplate periphery and bone periphery, such as in the posterior-medial portion to prevent deep-flexion component impingement, and in the anterior-lateral portion to avoid undue interaction between the anatomic iliotibial band and prosthesis components.

In one form thereof, the present invention provides a tibial prosthesis comprising: a distal surface; a proximal surface generally opposite the distal surface, the proximal surface having a lateral compartment and a medial compartment; and a peripheral wall extending between the distal and the proximal surface, the peripheral wall defining an anterior edge; a lateral posterior edge generally opposite the anterior edge and forming a posterior boundary of the lateral compartment; a medial posterior edge generally opposite the anterior edge and forming a posterior boundary of the medial compartment; a lateral periphery extending from the anterior edge to the lateral posterior edge, the lateral periphery defining a plurality of adjacent lateral arcs, an adjacent pair of the plurality of adjacent lateral arcs defining a first lateral radius and a second lateral radius, respectively, the first lateral radius larger than the second lateral radius by at least 100%, whereby the lateral periphery is relatively boxy; and a medial periphery extending from the anterior edge to the medial posterior edge, the medial periphery defining a plurality of adjacent medial arcs, an adjacent pair of the plurality of adjacent medial arcs defining a first medial radius and a second medial radius, respectively, the first medial radius larger than the second medial radius by less than 75%, whereby the medial periphery is generally rounded.

In another form thereof, the present invention provides a tibial prosthesis comprising: a distal surface; a proximal surface generally opposite the distal surface; and a peripheral wall extending between the distal and the proximal surface, the peripheral wall defining an anterior edge; a lateral periphery including: a lateral edge defining a substantially perpendicular tangent with respect to the anterior edge, an anterior-lateral corner traversing an angular sweep between the anterior edge and the lateral edge to define a boxy corner periphery having an anterior-lateral corner edge length, and a posterior-lateral corner extending away from the lateral edge and the anterior-lateral corner; and a medial periphery including: a medial edge defining a substantially perpendicular tangent with respect to the anterior edge, an anterior-medial corner traversing an angular sweep between the anterior edge and the medial edge to define a rounded corner periphery having an anterior-medial corner edge length that is longer than the anterior-lateral corner edge length, in which the angular sweep between the anterior edge and the medial edge is similar to the angular sweep between the anterior edge and the lateral edge, and a posterior-medial corner extending away from the medial edge and the anterior-medial corner.

In yet another form thereof, the present invention provides a tibial prosthesis comprising an asymmetric prosthesis periphery, the periphery comprising: an anteroposterior axis dividing the prosthesis periphery into a medial compartment and a lateral compartment; an anterior edge disposed between the medial compartment and the lateral compartment; a lateral posterior edge generally opposite the anterior edge and forming a posterior boundary of the lateral compartment; a medial posterior edge generally opposite the anterior edge and forming a posterior boundary of the medial compartment; a lateral periphery extending from the anterior edge to the lateral posterior edge, the lateral periphery defining: an anterior-lateral arc having an anterior-lateral arc center; and a lateral arc having a lateral arc center, the lateral arc defining a tangent parallel to the anteroposterior axis; a medial periphery extending from the anterior edge to the medial posterior edge, the medial periphery defining an anterior-medial arc having an anterior-medial arc center; and a medial arc having a medial arc center, the medial arc defining a tangent parallel to the anteroposterior axis, a mediolateral axis defining the longest line segment within the prosthesis periphery that is also perpendicular to the anteroposterior axis, the anterior-lateral arc center disposed between the mediolateral axis and the anterior edge, the anterior-medial arc center disposed posterior of the mediolateral axis.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 1B is an assembled, perspective view of the tibial baseplate and tibial bearing component shown in FIG. 1A;

FIG. 2A is a top plan view of the peripheries of a set of nine tibial baseplates made in accordance with the present disclosure, in which the peripheries are shown to scale according to the illustrated scales in millimeters in the bottom and right-hand margins of the page;

Corresponding reference characters indicate corresponding parts throughout the several views. The exemplifications set out herein illustrate exemplary embodiments of the invention, and such exemplifications are not to be construed as limiting the scope of the invention in any manner.

DETAILED DESCRIPTION

The present disclosure provides an asymmetric knee joint prosthesis which facilitates proper rotational and spatial orientation of a tibial baseplate and tibial bearing component upon a resected proximal tibia, while also offering large-area contact with the resected proximal tibia. The prosthesis permits a wide range of flexion motion, protects natural soft tissue proximate the knee joint prosthesis, and optimizes long term fixation characteristics of the prosthesis.

In order to prepare the tibia and femur for receipt of a knee joint prosthesis of the present disclosure, any suitable methods or apparatuses may be used. As used herein, "proximal" refers to a direction generally toward the torso of a patient, and "distal" refers to the opposite direction of proximal, i.e., away from the torso of the patient.

As used herein, the "periphery" of a tibial prosthesis refers to any periphery as viewed in a top plan view, e.g., in a generally transverse anatomical plane. Alternatively, the periphery of a tibial prosthesis may be any periphery as viewed in bottom plan view, e.g., in a generally transverse plane and looking at the distal surface adapted to contact a resected proximal surface of a tibial bone.

As used herein, the term "centroid" or "geometric center" refers to the intersection of all straight lines that divide a given area into two parts of equal moment about each respective line. Stated another way, a geometric center may be said to be the "average" (i.e., arithmetic mean) of all points of the given area. Stated yet another way, the geometric center is a point in a two dimensional figure from which the sum of the displacement vectors of all points on the figure equals zero.

As used herein, a "disparity" or "difference" between two numerical values (e.g., one value "larger" or "smaller" than another), typically expressed as a percentage, is the difference between the two values divided by the smaller of the two values. For example, a smaller quantity having value 75 and a larger quantity having value 150 would have a percentage disparity of (150-75)/75, or 100%.

Figure 5:
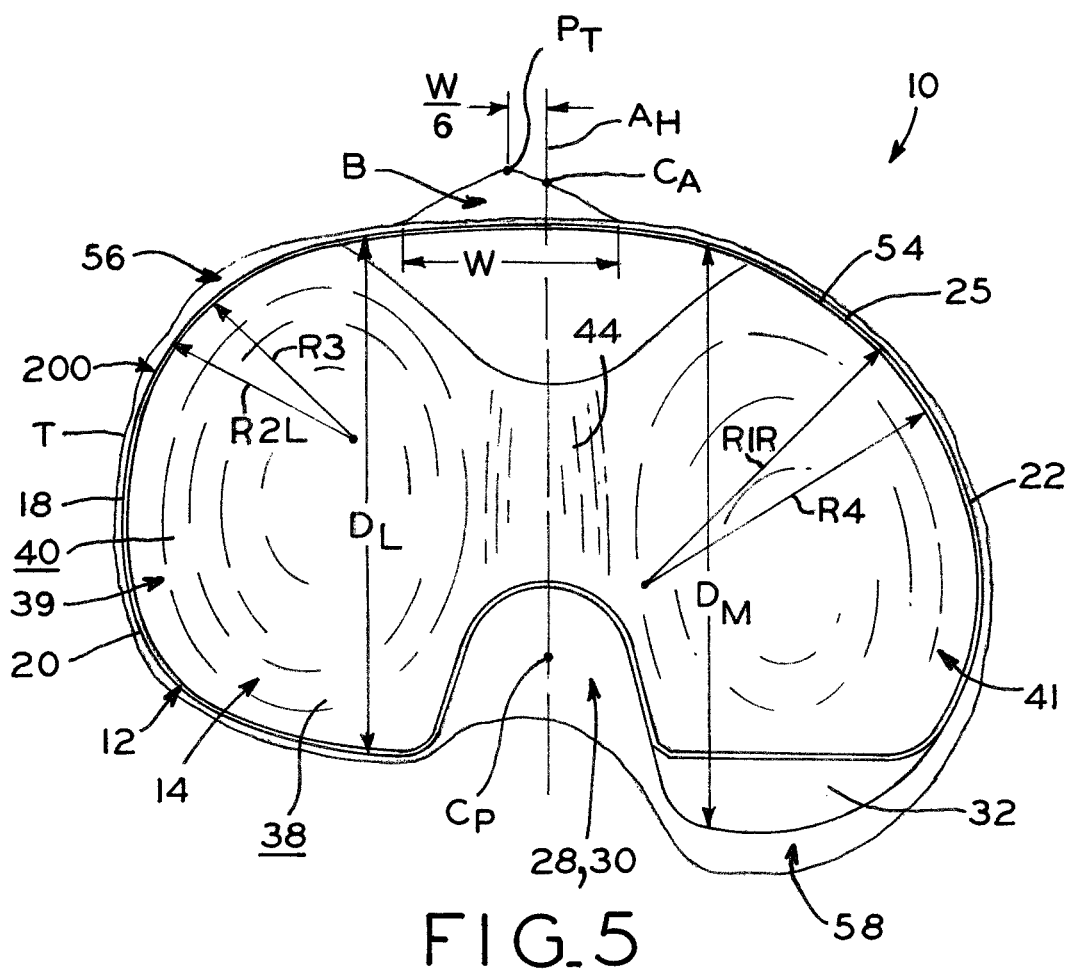
FIG. 5 is a top plan view of a resected proximal tibial surface with a prosthetic tibial baseplate component and tibial bearing component made in accordance with the present disclosure mounted thereon.

Referring to FIG. 5, tibia T includes tibial tubercle B having mediolateral width W, with tubercle midpoint $P_T$ located on tubercle B approximately halfway across width W. While tubercle B is shown as having midpoint $P_T$ at the "peak" or point of maximum anterior eminence, it is recognized that midpoint $P_T$ of tibia T may be spaced from such a peak. Tibia T also includes attachment point $C_P$ representing the geometric center of the attachment area between the anatomic posterior cruciate ligament (PCL) and tibia T. Recognizing that the PCL typically attaches to a tibia in two ligament "bundles," one of which is relatively anterior, lateral and proximal and the other of which relatively posterior, medial and distal, attachment point $C_P$ is contemplated as representing the anterior/lateral attachment area in an exemplary embodiment. However, it is contemplated that the posterior/medial attachment area, or the entire attachment area, could be used.

As used herein, "anterior" refers to a direction generally toward the front of a patient. "Posterior" refers to the opposite direction of anterior, i.e., toward the back of the patient.

In the context of patient anatomy, "home axis" $A_H$ refers to a generally anteroposterior axis extending from posterior point $C_P$ to an anterior point $C_A$, in which anterior point $C_A$ is disposed on tubercle B and medially spaced from tubercle midpoint $P_T$ by an amount equal to W/6. Stated another way, anterior point $C_A$ is laterally spaced by an amount equal to W/3 from the medial end of mediolateral width W, such that point $C_A$ lies on the "medial third" of the anterior tibial tubercle.

In the context of a prosthesis, such as tibial baseplate 12 described below, "home axis" $A_H$ refers to an axis oriented with respect to baseplate 12 such that the baseplate home axis $A_H$ of baseplate 12 is aligned with home axis $A_H$ of tibia T after implantation of baseplate 12 in a proper rotational and spatial orientation (as shown in FIG. 5). In the illustrative embodiments shown in FIG. 3 and described in detail below, home axis $A_H$ bisects PCL cutout 28 at the posterior edge of periphery 200 of tibial plateau 18 (FIG. 5), and bisects anterior edge 202 at the anterior edge of periphery 200 of tibial plateau 18. It is contemplated that home axis $A_H$ may be oriented to other baseplate features, it being understood home axis $A_H$ of baseplate 12 is positioned such that that proper alignment and orientation of baseplate 12 upon tibia T positions the home axis $A_H$ of baseplate 12 coincident with home axis $A_H$ of tibia T.

Home axis $A_H$ of tibial baseplate 12 may be said to be an anteroposterior axis, as home axis $A_H$ extends generally anteriorly and posteriorly when baseplate 12 is implanted upon tibia T. Tibial baseplate also defines mediolateral axis $A_{ML}$, which lies along the longest line segment contained within periphery 200 that is also perpendicular to home axis $A_H$ of baseplate 12. As described below, home axis $A_H$ and mediolateral axis $A_{ML}$ cooperate to define a coordinate system useful for quantifying certain baseplate features in accordance with the present disclosure.

Figure 1A:
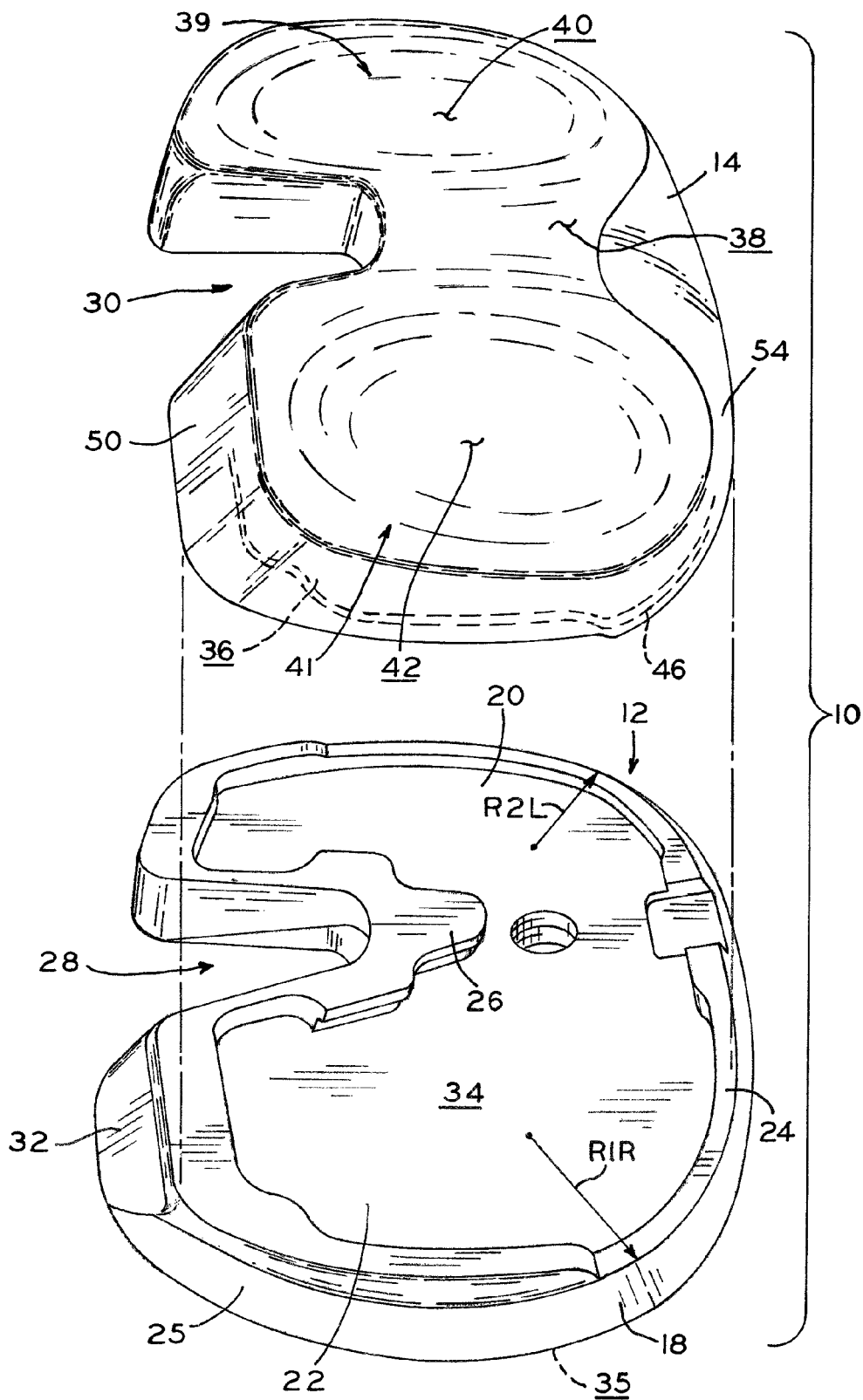
FIG. 1A is an exploded, perspective view of a tibial baseplate and tibial bearing component in accordance with the present disclosure.
Figure 2B:
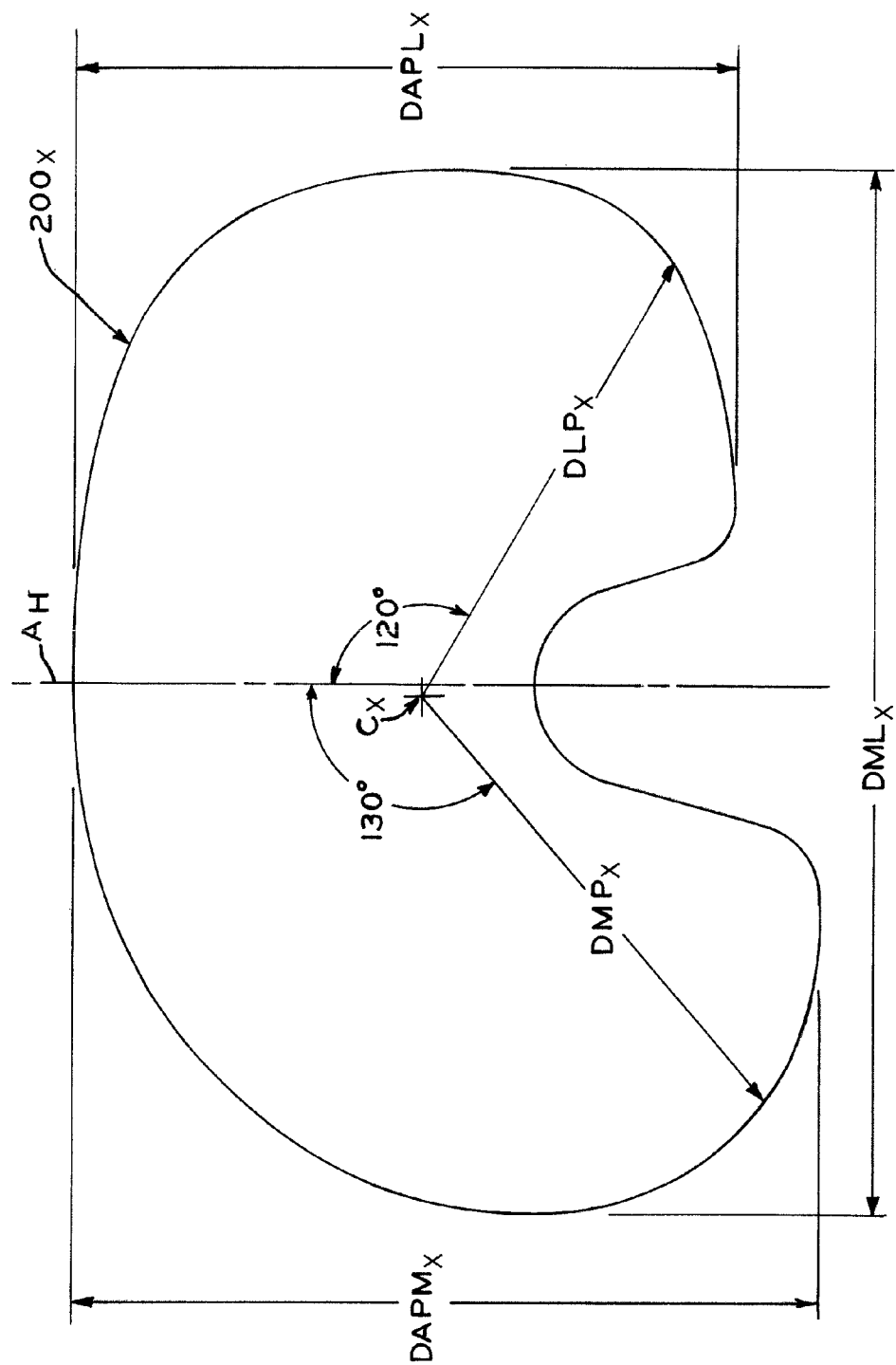
FIG. 2B is a top plan view of the periphery of a tibial baseplate made in accordance with the present disclosure.
Figure 3A:
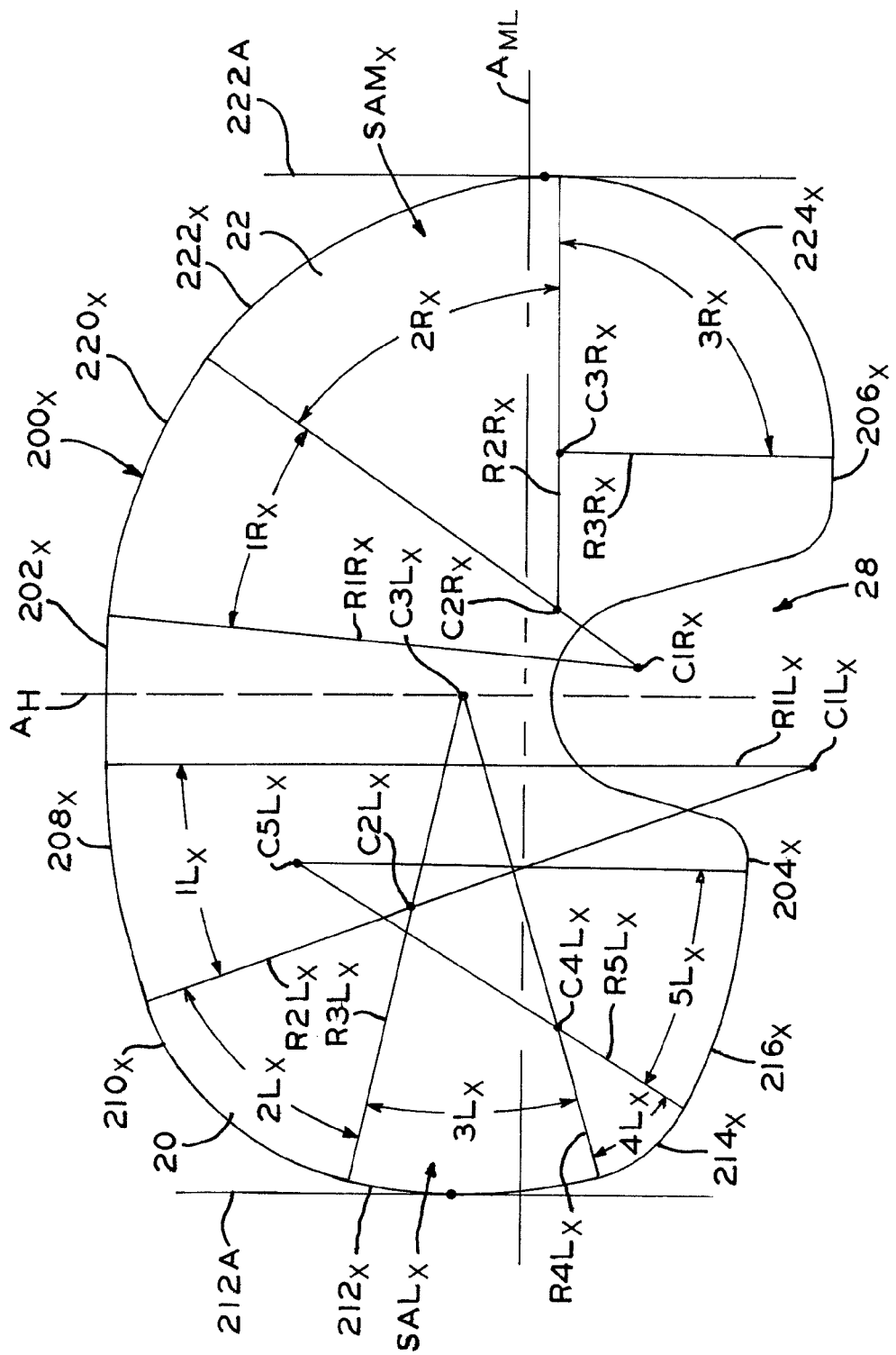
FIG. 3A is top plan view of a periphery of a tibial baseplate made in accordance with the present disclosure, illustrating various arcs defined by the periphery.
Figure 3B:
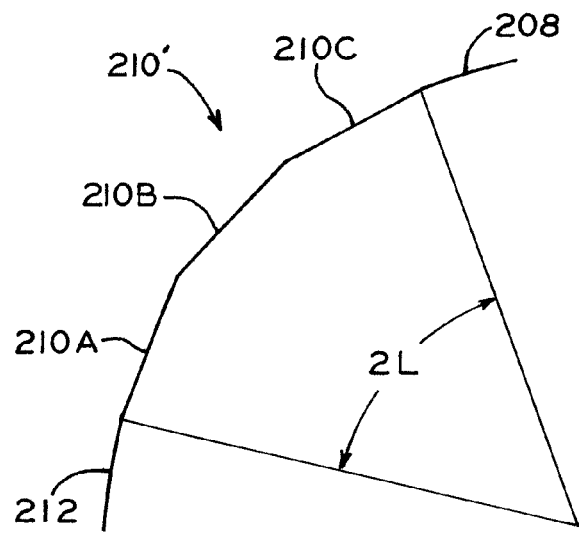
FIG. 3B is a partial, top plan view of the periphery shown in FIG. 3A, illustrating an alternative lateral corner periphery.
Figure 3C:
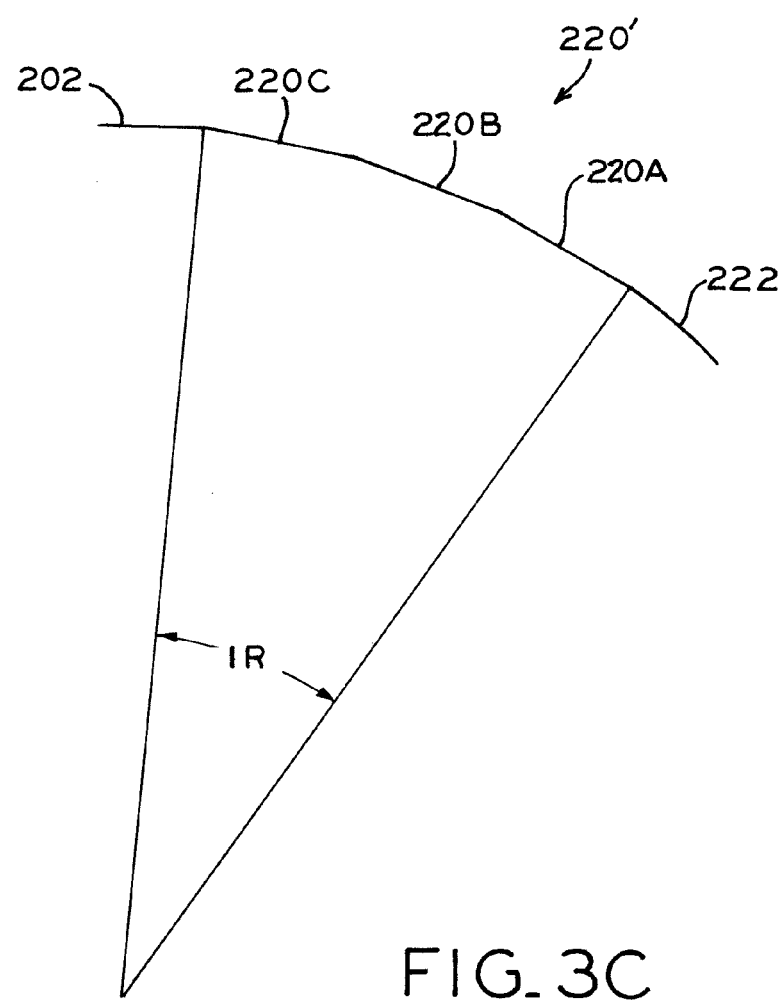
FIG. 3C is a partial, top plan view of the periphery shown in FIG. 3A, illustrating an alternative medial corner periphery.
Figure 3D:
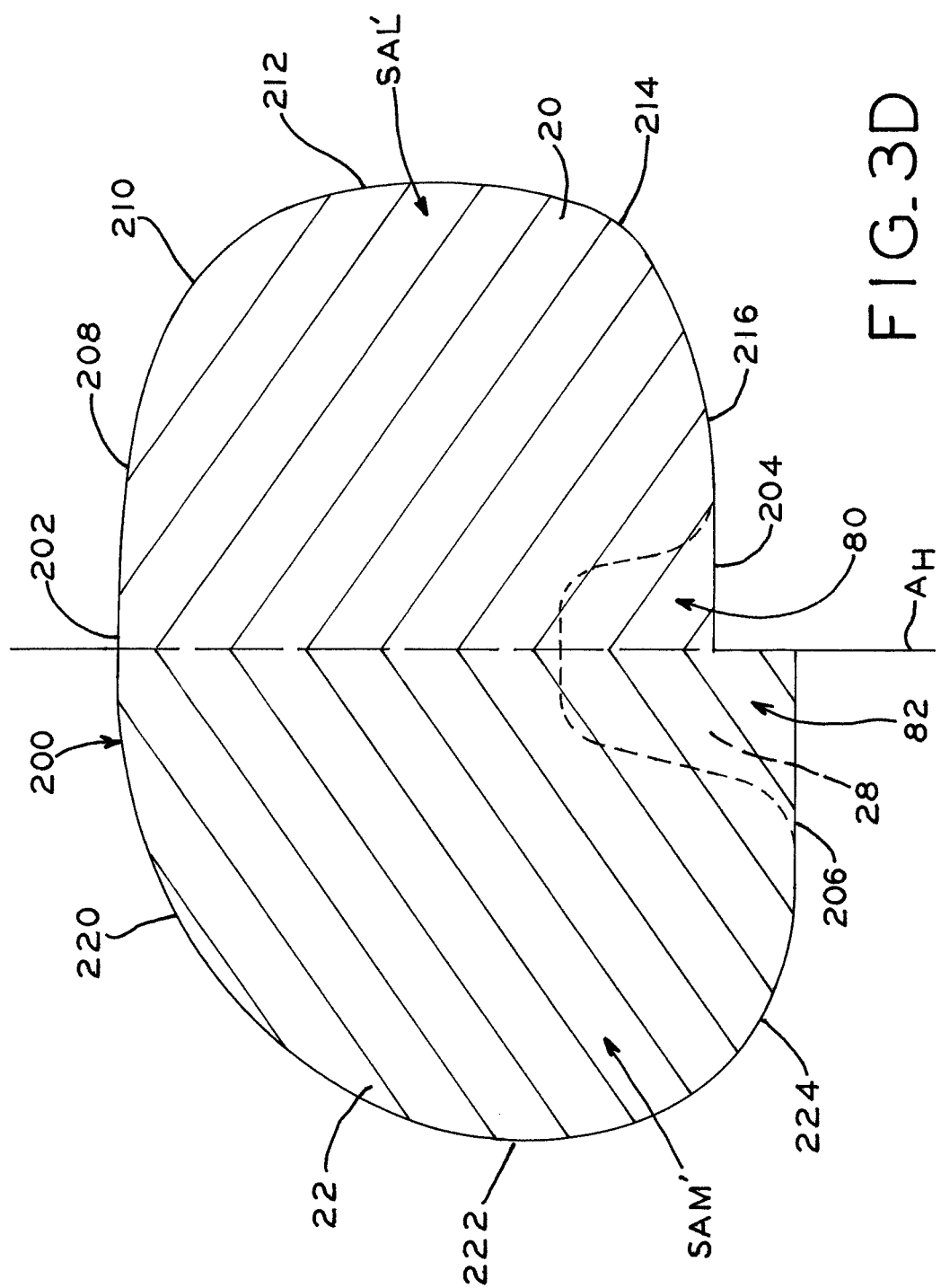
FIG. 3D is a top plan view of the periphery of a tibial baseplate made in accordance with the present disclosure, illustrating medial and lateral surface area calculations without a PCL cutout.
Figure 4A:
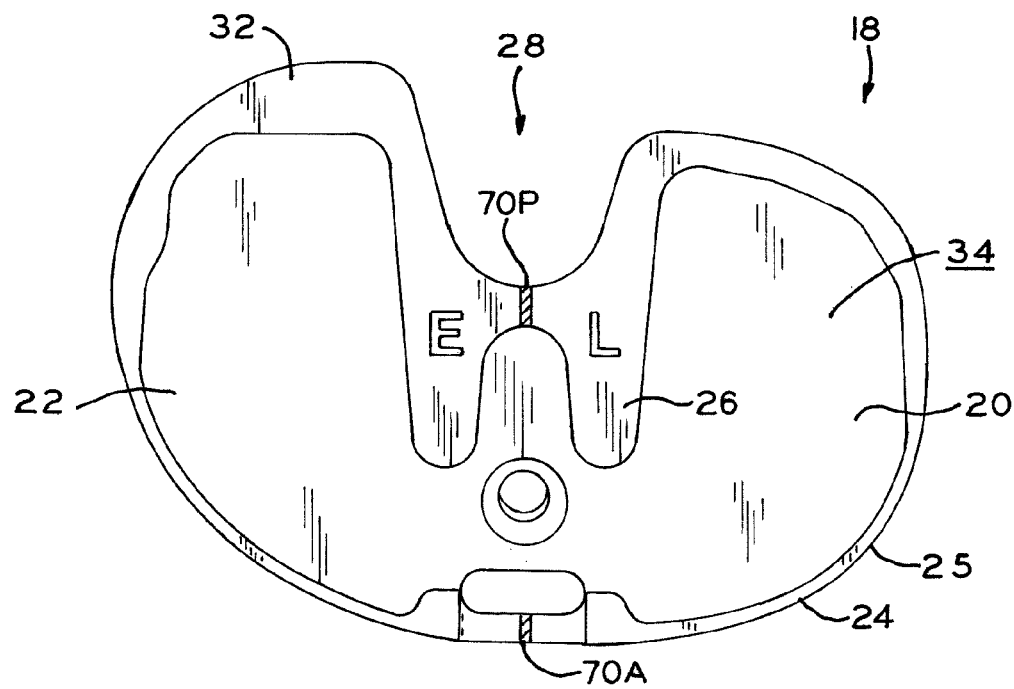
FIG. 4A is a top plan view of a tibial baseplate made in accordance with the present disclosure.
Figure 4B:
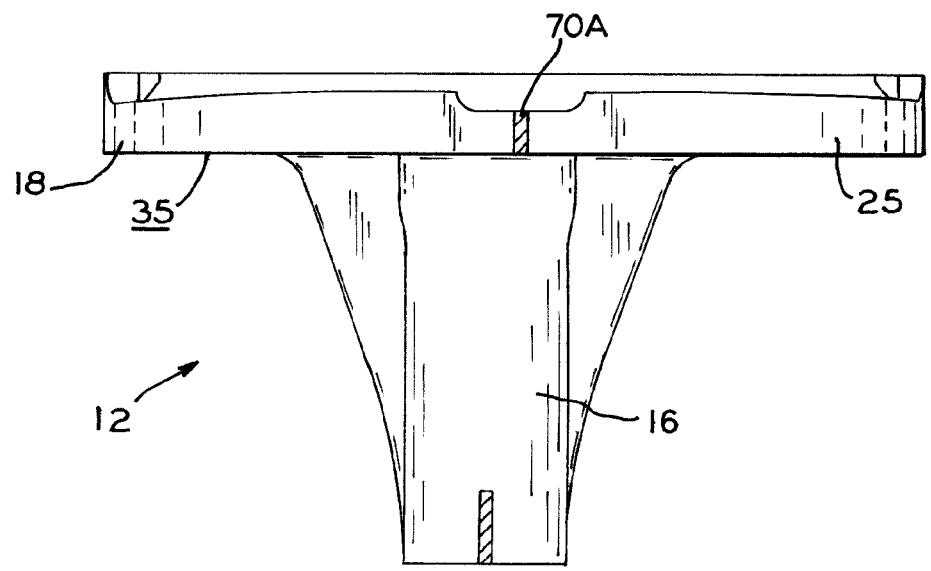
FIG. 4B is a side elevation view of the tibial baseplate shown in FIG. 4A.

The embodiments shown and described with regard to FIGS. 1A, 1B, 3A, 4A, 4B, 5 and 6 illustrate a left knee and associated features of a right-knee prosthesis, while the embodiments shown and described in FIGS. 2A, 2B and 3D illustrate the periphery of a right knee prosthesis. Right and left knee configurations are mirror images of one another about a sagittal plane. Thus, it will be appreciated that all aspects of the prosthesis described herein are equally applicable to a left- or right-knee configuration.

1. Asymmetry of the Tibial Prosthesis.

Referring now to FIGS. 1A and 1B, tibial prosthesis 10 includes tibial baseplate 12 and tibial bearing component 14. Tibial baseplate 12 may include a stem or keel 16 (FIG. 4B) extending distally from proximal tibial plateau 18, or may utilize other fixation structures for securing baseplate 12 to tibia T, such as distally extending pegs. Portions of the outer periphery defined by tibial plateau 18 closely correspond in size and shape with a resected proximal surface of tibia T, as described in detail below.

Tibial bearing component 14 and tibial baseplate 12 have a particular asymmetry, with respect to home axis $A_H$ (shown in FIG. 2A and described above), that is designed to maximize tibial coverage for a large proportion of knee-replacement candidates. This high level of coverage allows a surgeon to cover the largest possible area on the proximal resected surface of the tibia, which in turn offers maximum coverage of cortical bone. Advantageously, the maximized coverage of cortical bone facilitates superior support of tibial baseplate 12. A firm, enduring fixation of tibial baseplate 12 to tibia T is facilitated by large-area contact between the cortical and cancellous bone of tibia T and distal surface 35 of tibial plateau 18 (FIG. 4B), which may be coated with porous ingrowth material and/or bone cement.

In an analysis of a several human specimens, variations in size and geometry for a variety of anatomic tibial features were observed and characterized. Geometrical commonalities between anatomic features, or lack thereof, were noted. Mean tibial peripheral geometries were calculated based on statistical analysis and extrapolation of the collected anatomical data, in view of the observed geometrical commonalities organized around anatomic home axis $A_H$. These calculated mean geometries were categorized by tibial size.

A comparison between the asymmetric peripheries for the present family of prostheses and the calculated mean tibial geometries was conducted. Based on the results of this comparison, it has been found that substantial tibial coverage can be achieved for a large proportion of patients using tibial components having asymmetric peripheries in accordance with the present disclosure. Moreover, this coverage can be achieved with a relatively small number of sizes, even where particular portions of the prosthesis periphery is intentionally "pulled back" from the tibial periphery in order to confer other orthopaedic benefits. Further, the particular asymmetry of tibial baseplate 12 can be expected to offer such coverage without overhanging any portion of the resected surface.

Thus, periphery 200 including the particular asymmetric profile as described below confers the benefits of maximum coverage, facilitation of proper rotation (discussed below), and long-term fixation as described herein. Such asymmetry may be demonstrated in various ways, including: by a comparison of adjacent radii in the medial and lateral compartments of the asymmetric periphery; by a comparison of the edge length in anterior-medial and anterior lateral corners of the periphery, for a comparable lateral and medial angular sweep; and by a comparison of the location of radius centers for the anterior-medial and anterior-lateral corners with respect to a mediolateral axis. Various comparisons and quantifications are presented in detail below. Specific data and other geometric details of the peripheries for the various prosthesis sizes, from which the below-identified comparisons and quantifications are derived, may be obtained from the draw-to-scale peripheries shown in FIG. 2A.

Advantageously, the asymmetry of tibial component 12 encourages proper rotational orientation of baseplate 12 upon implantation thereof onto tibia T. As described in detail below, the asymmetry of periphery 200 (FIG. 2A) of tibial plateau 18 is designed to provide a close match in selected areas of the lateral and medial compartments as compared to the anatomic bone. As such, a surgeon can select the largest possible component from among a family of different component sizes, such that the component substantially covers the resected tibia T with minimal gaps between the tibial periphery and component periphery 200, as well as little or no overhang over any portions of the tibial periphery. Because the high congruence between prosthesis periphery 200 and the tibial periphery produces only a minimal gap between the peripheries (as shown in FIG. 5), tibial baseplate 12 cannot be rotated significantly without causing tibial plateau 18 to overhang beyond the periphery of the resected tibial surface. Thus, proper rotation of baseplate 12 can be ascertained by the visual acuity between prosthesis periphery 200 and the resected tibial surface.

The following examples and data are presented with respect to tibial baseplate 12. However, as described in more detail below, tibial bearing component 14 defines perimeter wall 54 which follows peripheral wall 25 of baseplate 12 except where noted. Thus, it is appreciated that the conclusions, trends and design features gleaned from data relating to the asymmetric periphery of tibial baseplate 12 also applies to the asymmetric periphery of tibial bearing component 14, except where stated otherwise.

Lateral compartment 20 and medial compartment 22 of tibial plateau 18 are dissimilar in size and shape, giving rise to the asymmetry thereof. This asymmetry is designed so that peripheral wall 25 traces the perimeter of the resected proximal surface of tibia T, such that tibial plateau 18 covers a large proportion of the resected proximal tibial surface as shown in FIG. 5. To achieve this large tibial coverage, tibial plateau 18 closely matches the periphery of tibia T in most areas as noted above. Nevertheless, as shown in FIG. 5, for example, a small gap between periphery 200 of tibial plateau 18 and tibia T is formed to allow some freedom of positioning and rotational orientation. The gap is designed to have a substantially continuous width in most areas, including the anterior edge, anterior-medial corner, medial edge, lateral edge and lateral-posterior corner (all described in detail below).

However, certain aspects of the asymmetric shape are designed to intentionally deviate from the calculated anatomical shape to confer particular features and advantages in the context of a complete, implanted knee prosthesis. Referring to FIG. 5, for example, tibial baseplate 12 and tibial bearing component 14 have anterior-lateral "corners" (described in detail below) which are "pulled back" to create gap 56 between tibia T and prosthesis 10 in the anterior-lateral area of the resected surface of tibia T. Advantageously, gap 56 creates extra space for "soft-tissue friendly" edges of prosthesis 10, thereby minimizing impingement of the iliotibial band. In an exemplary embodiment, gap 56 may range from 0.5 mm for a small-size prosthesis (such as size 1/A described below), to 1 mm for a medium-sized prosthesis (such as size 5/E described below), to 2 mm for a large-sized prosthesis (such as size 9/J described below).

Similarly, the posterior edge of the medial compartment may be "pulled back" from the adjacent edge of tibia T to define gap 58. Gap 58 allows extra space for adjacent soft tissues, particularly in deep flexion as described below. Gap 58 also allows prosthesis 10 to be rotated about a lateral pivot by a small amount, thereby offering a surgeon the freedom to displace medial compartment 22 posteriorly as required or desired for a particular patient. In an exemplary embodiment, gap 58 is about 4 mm.

Figure 8:
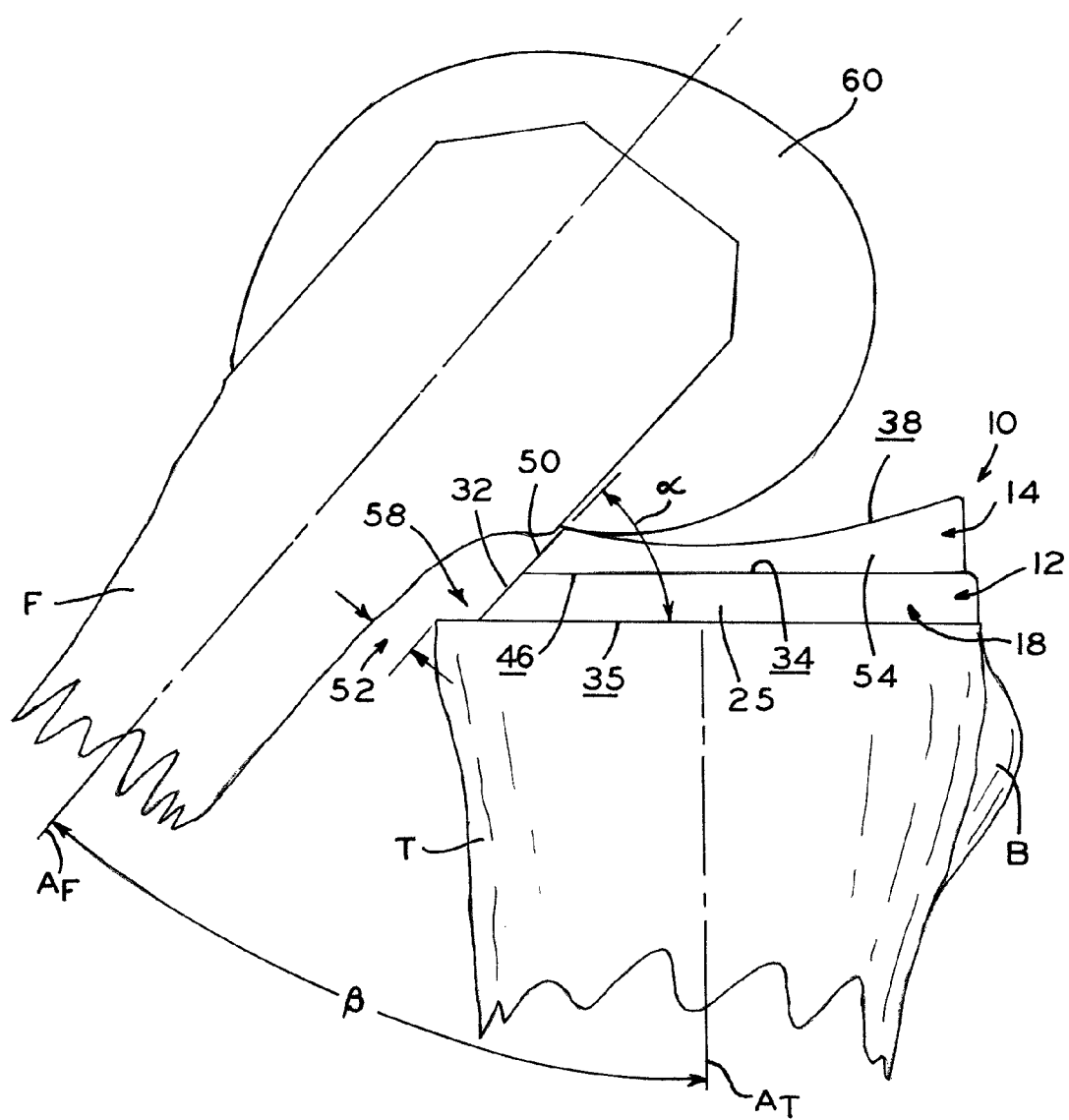
FIG. 8 is a side, elevation view of the tibial components shown in FIG. 1A, in conjunction with a femoral component.

As described in detail below, the asymmetrical periphery also provides a large overall area for proximal surface 34 of baseplate 12, which creates sufficient space for large contact areas between tibial bearing component 14 and femoral component 60 (FIG. 8).

a. Medial/Lateral Peripheral Curvatures

The particular asymmetric shape of tibial plateau 18 (and of tibial bearing component 14, which defines a similar periphery as described below) gives rise to a generally "boxy" or angular periphery in lateral compartment 20, and a "rounded" or soft periphery in medial compartment 22.

Turning to FIG. 3A, the periphery 200 of tibial plateau 18 surrounds lateral compartment 20 and medial compartment 22, each of which define a plurality of lateral and medial arcs extending between anterior edge 202 and lateral and medial posterior edges 204, 206 respectively. In the illustrative embodiment of FIG. 3A, anterior edge 202, lateral posterior edge 204 and medial posterior edge 206 are substantially planar and parallel for ease of reference. However, it is contemplated that edges 202, 204, 206 may take on other shapes and configurations within the scope of the present disclosure, such as angled or arcuate.

In the exemplary embodiment of FIG. 3A, lateral compartment 20 includes five separate arcs including lateral anterior edge arc 208, anterior-lateral corner arc 210, lateral edge arc 212, posterior-lateral corner arc 214, and lateral posterior edge arc 216. Each of lateral arcs 208, 210, 212, 214 and 216 defines angular sweep 1L, 2L, 3L, 4L and 5L, respectively, having radii R1L, R2L, R3L, R4L and R5L respectively. A radius of a particular angular sweep extends from the respective radius center (i.e., one of centers C1L, C2L, C3L, C4L and C5L) to periphery 200. Radii R1L, R2L, R3L, R4L and R5L each remain unchanged throughout the extent of angular sweeps 1L, 2L, 3L, 4L and 5L, respectively.

Similarly, medial compartment 22 includes three separate arcs including anterior-medial corner arc 220, medial edge arc 222 and posterior-lateral corner arc 224, defining angular sweeps 1R, 2R and 3R, respectively having radii R1R, R2R and R3R respectively.

In FIG. 2A, peripheries $200_X$ are shown for each of nine progressively larger component sizes, with $200_1$ being the periphery of the smallest size (size "1" or "A") and $200_9$ being the periphery of the largest size (size "9" or "J"). For purposes of the present disclosure, several quantities and features of tibial baseplate 12 may be described with the subscript "X" appearing after the reference numeral corresponding to a component size as set for in the Tables, Figures and description below. The subscript "X" indicates that the reference numeral applies to all nine differently-sized embodiments described and shown herein.

In exemplary embodiments, medial and lateral radii may be any value within the following ranges: for medial radius $R1R_X$, between about 27 mm and about 47 mm; for medial radius $R2R_X$, between about 21 mm and about 49 mm; for medial radius $R3R_X$, between about 14 mm and about 31 mm; for lateral radius $R1L_X$, between about 46 mm and about 59 mm; for lateral radius $R2L_X$, between about 13 mm and about 27 mm; for lateral radius $R3L_X$ between about 27 mm and about 46 mm; for lateral radius $R4L_X$ between about 6 mm and about 14 mm; and for lateral radius $R5L_X$ between about 22 mm and about 35 mm.

In exemplary embodiments, medial and lateral angular extents or sweeps may be any value within the following ranges: for medial angle $1R_X$, between about 13 degrees and about 71 degrees; for medial angle $2R_X$, between about 23 degrees and about 67 degrees; for medial angle $3R_X$, between about 23 degrees and about 90 degrees; for lateral angle $1L_X$, between about 11 degrees and about 32 degrees; for lateral angle $2L_X$, between about 42 degrees and about 63 degrees; for lateral angle $3L_X$, between about 23 degrees and about 47 degrees; for lateral angle $4L_X$, between about 36 degrees and about 46 degrees; and for lateral angle $5L_X$, between about 28 degrees and about 67 degrees;

The unique asymmetry of periphery 200 defined by tibial plateau 18 can be quantified in multiple ways with respect to the curvatures of lateral and medial compartments 20 and 22 as defined by the arrangement and geometry of lateral arcs 208, 210, 212, 214, 216 and medial arcs 220, 222, 224.

One measure of the asymmetry of periphery 200 is found in a simple comparison of radii R2L and R1R, which are the anterior "corner" radii of lateral and medial compartments 20 and 22 respectively. Generally speaking, a corner of a baseplate periphery may be said to be that portion of the periphery where a transition from an anterior or posterior edge to a lateral or medial edge occurs. For example, in the illustrative embodiment of FIG. 3A, the anterior-lateral corner is principally occupied by anterior-lateral corner arc 210, which defines a substantially medial-lateral tangent at the anterior end of arc 210 and a substantially anteroposterior tangent at the lateral end of arc 210. Similarly, the medial corner of periphery 200 is principally occupied by anterior-medial corner arc 220, which defines a substantially medial-lateral tangent at the anterior end of arc 220 and a more anteroposterior tangent at the lateral end of arc 220. For some purposes, the anterior-medial corner of periphery 200 may be said to include a portion of medial edge arc 222, as described below.

A periphery corner may also be defined by a particular angular sweep with respect to an anteroposterior reference axis. Such reference axis may extend posteriorly from an anterior-most point of a tibial prosthesis (e.g., from the center of anterior edge 202 of periphery 200) to divide the prosthesis into medial and lateral halves. In a symmetrical prosthesis, the anteroposterior reference axis is the axis of symmetry.

In the illustrative embodiment of FIG. 3A, the anteroposterior reference axis may be home axis $A_H$, such that the anterior-medial corner of periphery 200 occupies some or all of the 90-degree clockwise angular sweep between home axis $A_H$ (at zero degrees, i.e., the beginning of the clockwise sweep) and mediolateral axis $A_{ML}$ (at 90 degrees, i.e., the end of the sweep). Similarly, the anterior-lateral corner of periphery 200 occupies some or all of the 90-degree counter-clockwise angular sweep between home axis $A_H$ and mediolateral axis $A_{ML}$.

For example, the anterior-medial and anterior-lateral corners may each occupy the central 45 degree angular sweep of their respective 90-degree angular sweeps as described above. Thus, the anterior-lateral corner of periphery 200 would begin at a position rotated 22.5 degrees counter-clockwise from home axis $A_H$ as described above, and would end at 67.5 degrees counter-clockwise from home axis $A_H$. Similarly, the anterior-medial corner would begin at a 22.5-degree clockwise rotation and end at a 67.5 degree clockwise rotation.

It is contemplated that the anterior-lateral and anterior-medial corners may occupy any angular sweep as required or desired for a particular design. For purposes of comparison between two corners in a given prosthesis periphery, however, a comparable angular sweep for the lateral and medial sides is envisioned, i.e., the extent and location of the compared angles may be "mirror images" of one another about an anteroposterior axis. For example, in a comparison of anterior-lateral and anterior-medial radii R2L, R1R, it is contemplated that such comparison is calculated across lateral and medial angular sweeps which each begin and end at similar angular end points with respect to the chosen reference axis (e.g., home axis $A_H$).

As best seen in FIGS. 3A and 5, one aspect of the asymmetric periphery of baseplate 12 arises from $R1R_X$ being substantially larger than $R2L_X$. Table 1, below, also includes a comparison of radii $R1R_X$ and $R2L_X$ across nine exemplary component sizes, demonstrating that difference Δ-12RL between radius $R1R_X$ and radius $R2L_X$ may be as little as 48%, 76% or 78%, and may be as much as 102%, 103% or 149%. It is contemplated that radius $R1R_X$ may be larger than radius $R2L_X$ by any percentage value within any range defined by the listed values.

TABLE 1

Comparisons of Values of Respective Medial and Lateral Anterior Corner Radii

| SIZE | Δ-12RL<br>R1R vs. R2L |
|---|---|
| 1/A | 103.0% |
| 2/B | 149.2% |
| 3/C | 82.4% |
| 4/D | 74.6% |
| 5/E | 90.9% |
| 6/F | 78.6% |
| 7/G | 102.2% |
| 8/H | 86.5% |
| 9/J | 48.1% |
| AVG | 90.6% |

All Δ values are expressed as the difference between a given pair of radii, expressed as a percentage of the smaller of the two radii Stated another way, the smaller $R2L_X$ makes a sharper turn, thereby imparting a relatively more "boxy" appearance to the anterior corner of lateral compartment 20, while the relatively larger radius $R1R_X$ makes a more gradual turn that imparts a more "rounded" appearance to the anterior corner of medial compartment 22. In the exemplary nine sizes illustrated in FIG. 2A and shown in Table 1, an average disparity between the lateral and medial anterior corner radii $R2L_X$ and $R1R_X$ is greater than 90%. In some sizes of periphery $200_X$, the anterior-medial "corner" making the more gradual turn may also includes medial edge arc 222.

As described in detail below, this "rounded-medial/boxy-lateral" asymmetry of the anterior corners of tibial plateau facilitates and encourages proper rotational orientation and positioning of baseplate 12 upon tibia T upon implantation by allowing periphery 200 to closely match the periphery of a typical resected tibia T (FIG. 5), while also maximizing the surface area of proximal surface 34 of tibial plateau to allow for use of a tibial bearing component 14 with a concomitantly large proximal surface area.

As noted above, the small-radius "corner" defined by angle 2L may be considered to have a similar angular sweep as a large-radius "corner" defined by angles 1R, 2R (or a combination of portions thereof) for purposes of comparing the two radii. Given this comparable angular sweep, another measure of the asymmetry defined by the medial and lateral anterior corners is the arc length of the corners. More particularly, because medial radii $R1R_X$ and $R2R_X$ are larger than lateral radius $R2L_X$ (as described above), it follows that the medial corner has a larger arc length as compared to the lateral corner arc length for a given angular sweep.

Moreover, while the peripheries of lateral and medial compartments 20, 22 are shown as being generally rounded and therefore defining respective radii, it is contemplated that an asymmetric periphery in accordance with the present disclosure need not define a radius per se, but rather could include one or more straight line segments which, on the whole, define asymmetric corner edge lengths in the medial and lateral compartments. Referring to FIG. 3B, for example, it is contemplated that an alternative anterior lateral corner 210' could be comprised of three line segments 210A, 210B, 210C which cooperate to span angular extent 2L. Similarly, an alternative anterior medial corner 220' could be comprised of three line segments 220A, 220B, 220C which cooperate to span angular extent 1R. Any of the other arcs which define periphery 200 could be similarly configured as one or more line segments. In the variant illustrated by FIGS. 3B and 3C, the difference between corner radii would not be an appropriate measure of asymmetry because the straight line segments would not define radii. Asymmetry of the medial and lateral anterior corners would instead be quantified by comparison of the respective lengths of the medial and lateral corner edges across comparable medial and lateral angular extents.

Yet another way to quantify the asymmetry of the anterior corner arcs (i.e., anterior-lateral corner arc 210 and anterior-medial corner arc 220) is to compare the distance of the lateral and medial radius centers C2L and C1R respectively, from anterior edge 202 and/or mediolateral axis $A_{ML}$ (FIG. 3A). In the boxy anterior-lateral corner, center C2L$_X$ of radius R2L$_X$ is anterior of mediolateral axis $A_{ML}$ and relatively close to anterior edge 202. For the rounded, anterior-medial corner, centers C1R$_X$ and C2R$_X$ of radii R1R$_X$ and R2R$_X$, respectively, are posterior of mediolateral axis $A_{ML}$ and relatively far from anterior edge 202.

Another metric for quantifying the "boxy vs. rounded" asymmetry of periphery 200 is a comparison between ratios of adjacent radii. In the more boxy lateral compartment 20, pairs of adjacent radii define large ratios because the large edge radii (i.e., of lateral anterior edge arc 208, lateral edge arc 212 and lateral posterior edge arc 216) are much larger than the adjacent corner radii (i.e., of anterior-lateral corner arc 210 and posterior-lateral corner arc 214). On the other hand, in the more rounded medial compartment 22, pairs of adjacent radii define small ratios (i.e., nearly 1:1) because the radii of the medial arcs (i.e., anterior-medial corner arc 220, medial edge arc 222 and posterior-medial corner arc 224) are of similar magnitude.

In the illustrated embodiment of FIG. 3A, lateral edge arc 212 is considered an "edge" because arc 212 defines tangent 212A which is substantially perpendicular to anterior edge 202. Just as a "corner" may be considered to be the portion of periphery 200 which makes a transition from anterior or posterior to medial or lateral, an edge is that portion of periphery 200 which encompasses the anterior, posterior, medial or lateral terminus of periphery 200.

Similarly, medial edge arc 222 defines tangent 222A which is also substantially perpendicular to anterior edge 202. The medial "edge" of periphery 200 may be part of the same arc that extends around the anterior-medial corner and/or the anterior-lateral corner, as the medial arcs are similar. Indeed, as noted herein, medial compartment 22 may have a single arc which extends from anterior edge 202 to medial posterior edge 206.

Table 2 shows a comparison between adjacent-radii ratios for lateral and medial compartments 20 and 22. For each adjacent pair of radii, the difference between the radii magnitudes are expressed as a percentage of the smaller radius of the pair, as noted above.

TABLE 2

Comparisons of Values of Respective Pairs of Baseplate Peripheral Radii

| SIZE | Δ-12R R1R vs. R2R | Δ-23R R2R vs. R3R | Δ-12L R1L vs. R2L | Δ-23L R2L vs. R3L | Δ-34L R3L vs. R4L | Δ-45L R4L vs. R5L |
|---|---|---|---|---|---|---|
| 1/A | 18.3% | 58.6% | 337.3% | 141.8% | 323.5% | 194.1% |
| 2/B | 49.0% | 62.0% | 254.1% | 96.7% | 361.5% | 315.4% |
| 3/C | 24.0% | 48.8% | 247.1% | 58.8% | 203.4% | 214.6% |
| 4/D | 44.2% | 34.4% | 207.0% | 59.2% | 213.9% | 244.4% |
| 5/E | 23.3% | 57.9% | 151.5% | 80.6% | 250.0% | 250.0% |
| 6/F | 46.5% | 37.6% | 122.6% | 42.9% | 222.6% | 260.2% |

TABLE 2-continued

Comparisons of Values of Respective Pairs of Baseplate Peripheral Radii

| SIZE | Δ-12R R1R vs. R2R | Δ-23R R2R vs. R3R | Δ-12L R1L vs. R2L | Δ-23L R2L vs. R3L | Δ-34L R3L vs. R4L | Δ-45L R4L vs. R5L |
|---|---|---|---|---|---|---|
| 7/G | 25.3% | 38.9% | 110.8% | 64.5% | 264.3% | 176.2% |
| 8/H | 73.6% | 21.3% | 109.0% | 80.9% | 198.1% | 142.6% |
| 9/J | 21.9% | 61.2% | 70.4% | 68.5% | 264.0% | 172.0% |
| AVG | 36.2% | 46.7% | 178.9% | 77.1% | 255.7% | 218.8% |

All Δ values are expressed as the difference between a given pair of radii, expressed as a percentage of the smaller of the two radii As illustrated in Table 2, the "boxy" periphery of lateral compartment 20 gives rise to disparity values Δ-12L, Δ-23L, Δ-34L and Δ-45L that are at least 42%, 48% or 59%, and as great as 323%, 337% or 362%. It is contemplated that the disparity between a pair of adjacent radii in the boxy periphery of lateral compartment 20 may be any percentage value within any range defined by any of the listed values. It is also contemplated that the lateral disparity values may be substantially higher, as required or desired for a particular application.

Meanwhile, the "rounded" periphery of medial compartment 22 gives rise to disparity values Δ-12R and Δ-23R that are as small as 21%, 23% or 25%, and no greater than 61%, 62% or 74%. It is contemplated that the disparity between a pair of adjacent radii in the rounded periphery of medial compartment 22 may be any value within any range defined by any of the listed values. It is also contemplated that the medial disparity values may be less than 21%, and as little as zero %, as required or desired for a particular application.

Moreover, the boxy shape of lateral compartment 20 and rounded shape of medial compartment 22 is also demonstrated by the number of arcs used to define the portion of periphery 200 in lateral and medial compartments 20, 22. In lateral compartment 20, five arcs (i.e., arcs 208, 210, 212, 204, 216) are used to define the lateral periphery, which is indicative of anterior, lateral and posterior "sides" of a box joined by the relatively sharp transitions of corner arcs 210, 214. On the other hand, medial compartment 22 uses only three radii (i.e., 220, 222, 224), leaving no clear definition of any box "sides" or other transitions. Indeed, it is contemplated that medial compartment 22 could join anterior edge 202 to medial posterior edge 206 by a single radius within the scope of the present disclosure.

b. Surface Area of Medial and Lateral Baseplate Compartments

Referring still to FIG. 3A, yet another characterization of the asymmetry of periphery 200 arises from disparities in surface area for lateral and medial compartments 20, 22. For purposes of the present disclosure, surface area of lateral compartment SAL is that area contained within periphery 200, and on the lateral side of home axis $A_H$. Similarly, the surface area of medial compartment 22 is that area contained within periphery 200, and on the medial side of home axis $A_H$.

In an exemplary embodiment, lateral surface area SAL$_X$ may be as little as 844 mm$^2$ or may be as much as 1892 mm$^2$, or may be any area within the range defined by the foregoing values. In an exemplary embodiment, medial surface area SAM$_X$ may be as little as 899 mm$^2$ or may be as much as 2140 mm$^2$, or may be any area within the range defined by the foregoing values.

Surfaces areas SAL and SAM do not include any of the area occupied by PCL cutout 28, as any such area is not within periphery 200. However, the asymmetry of surface areas SAL and SAM arises primarily from the differences in the geometry and placement of arcs 208, 210, 212, 214, 216, 220, 222, 224 rather than from any asymmetry of PCL cutout 28. In the illustrative embodiments of FIG. 2A, for example, PCL cutout $28_X$ is symmetrical with respect to home axis $A_H$, but extends further posteriorly in medial compartment 22.

Thus, it is contemplated that the asymmetry of surfaces areas SAL, SAM are little changed by exclusion of the PCL cutout 28 from the area calculation. As illustrated in FIG. 3D, PCL cutout 28 is effectively excluded from calculation by extrapolating the line formed by lateral posterior edge 204 and medial posterior edge 206 inwardly to intersect with home axis $A_H$. In lateral compartment 20, such extrapolation cooperates with the lateral side of PCL cutout 28 to define lateral fill area 80. In medial compartment 22, such extrapolation cooperates with the medial side of PCL cutout 28 to define medial fill area 82.

In the illustrative embodiment of FIG. 3D, lateral surface area $SAL_X$' may be as little as 892 mm² or may be as much as 2066 mm², or may be any area within the range defined by the foregoing values. In an exemplary embodiment, medial surface area $SAM_X$' may be as little as 986 mm² or may be as much as 2404 mm², or may be any area within the range defined by the foregoing values.

Tables 3 and 4 below illustrate that medial surface area $SAM_X$ occupies a greater percentage of the total surface area contained within periphery $200_X$, regardless of whether PCL cutout 28 is included in the calculation. That is to say, medial fill area 82 is larger than lateral fill area 80 by approximately the same proportion as medial and lateral surfaces areas $SAM_X$, $SAL_X$. In the exemplary embodiments of FIG. 3A, medial surface area $SAM_X$ occupies between 52% and 53% of the total surface area regardless, while lateral surface area $SAM_X$ occupies the remainder. If the PCL cutout is excluded from the calculation as shown in FIG. 3D, medial surface area $SAM_X$' occupies between 52% and 54% of the total surface area, while lateral surface area $SAM_X$' occupies the remainder. With or without the PCL cutout included in the calculation, it is contemplated that medial surface areas $SAM_X$, $SAM_X$' may occupy as little as 51% of the total surface area, and as much as 60% of the total surface area.

TABLE 3

Medial vs. Lateral Tibial Baseplate Surface
Areas for Baseplates with a PCL Cutout
(FIGS. 2A and 3A)
With PCL Notch

| Size | Medial Surface Area $SAM_X$ as % of Total Surface Area |
|---|---|
| 1/A | 52% |
| 2/B | 52% |
| 3/C | 52% |
| 4/D | 52% |
| 5/E | 52% |
| 6/F | 52% |
| 7/G | 53% |
| 8/H | 53% |
| 9/J | 53% |

TABLE 4

Medial vs. Lateral Tibial Baseplate Surface
Areas for Baseplates without a PCL Cutout
(FIG. 3D)
Without PCL Notch

| Size | Medial Surface Area $SAM_X$' as % of Total Surface Area |
|---|---|
| 1/A | 53% |
| 2/B | 52% |
| 3/C | 53% |
| 4/D | 53% |
| 5/E | 53% |
| 6/F | 53% |
| 7/G | 53% |
| 8/H | 54% |
| 9/J | 54% | c. Anteroposterior Extent of Medial and Lateral Compartments

Still another way to characterize and quantify the asymmetry of tibial periphery 200 is to compare the overall anteroposterior extent of lateral and medial compartments 20, 22.

Turning to FIG. 2A (which is drawn to scale, according to scales 230 and 232) and FIG. 2B, lateral compartment 20 of tibial plateau 18 defines overall lateral anteroposterior extent $DAPL_X$, while medial compartment 22 of tibial plateau 18 defines overall medial anteroposterior extent $DAPM_X$, where X is an integer between 1 and 9 corresponding to a particular component size as shown in FIG. 2A, as noted above. As illustrated in Table 5 below, lateral anteroposterior extent $DAPL_X$ is less than medial anteroposterior extent $DAPM_X$, for all component sizes.

This disparity in anteroposterior extent can be said to result from medial compartment 22 extending posteriorly further than lateral compartment 20. In the illustrative embodiment of FIG. 2B, lateral anteroposterior extent $DAPL_X$ extends from anterior edge 202 to lateral posterior edge 204, while medial anteroposterior extent $DAPM_X$ extends from anterior edge 202 to medial posterior edge 206. Thus, if one takes anterior edge 202 to be the anteroposterior "zero point," the additional anteroposterior extent defined by medial compartment 22 is due entirely to the further posterior position of medial posterior edge 206.

As set forth in the right-hand column of Table 5, exemplary embodiments of tibial baseplate 12 may define medial anteroposterior extent $DAPM_X$ that is larger than lateral anteroposterior extent $DAPL_X$ by as little as 12.1%, 12.2% or 12.4%, and as much as 13.7%, 14.2% or 14.5%. It is contemplated that such disparity between medial and lateral anteroposterior extents $DAPM_X$, $DAPL_X$ may be any percentage within any range defined by the listed values of Table 5. Advantageously, the particular asymmetric arrangement of tibial baseplate 12 with respect to anteroposterior extent of lateral and medial compartments 20, 22 facilitates substantially complete coverage of tibia T, without overhanging the edge of tibia T, in a wide variety of patients.

TABLE 5

Overall A/P and M/L Dimensions for Tibial Baseplates
(FIGS. 2A and 2B)

| Size (X) | Growth in A/P Medial Dimension (DAPM), from next-smaller size, mm | Growth in A/P Lateral Dimension (DAPL), from next-smaller size, mm | Additional A/P Extent of DAPM vs. DAPL, % of DAPL |
|---|---|---|---|
| 1/A | — | — | 14.5% |
| 2/B | 2.3 | 2.13 | 14.2% |
| 3/C | 2.4 | 2.25 | 13.7% |

TABLE 5-continued

Overall A/P and M/L Dimensions for Tibial Baseplates
(FIGS. 2A and 2B)

| Size (X) | Growth in A/P Medial Dimension (DAPM), from next-smaller size, mm | Growth in A/P Lateral Dimension (DAPL), from next-smaller size, mm | Additional A/P Extent of DAPM vs. DAPL, % of DAPL |
|---|---|---|---|
| 4/D | 2.3 | 2.27 | 13.1% |
| 5/E | 3 | 2.8 | 12.7% |
| 6/F | 3.1 | 2.85 | 12.4% |
| 7/G | 3.2 | 2.81 | 12.5% |
| 8/H | 3.3 | 3.11 | 12.2% |
| 9/J | 3.73 | 3.34 | 12.1% |

For example, in an exemplary family of prosthesis sizes, at least 60% and as much as 90% coverage of the resected proximal surface is provided by tibial plateau 18 of tibial baseplate 12 when rotation is limited to +/−5 degrees from home axis $A_H$. In a majority of all patients, such coverage is between 75-85%. Coverage of up to 100% may be achieved within the scope of the present disclosure, such as by fully extending the posterior-medial and anterior-lateral coverage of tibial plateau (which intentionally leave gaps between tibial plateau 18 and the periphery of tibia T as noted herein).

The additional posteromedial material of tibial plateau 18 includes chamfer 32, described in detail below with respect to the assembly of tibial baseplate 12 to tibial bearing component 14. Chamfer 32 is formed in peripheral wall 25, such that chamfer 32 forms angle α (FIG. 8) with the distal or bone-contacting surface 35 of tibial plateau 18. In the illustrated embodiment, chamfer 32 defines a substantially linear sagittal cross-sectional profile, with angle α between about 35 degrees and about 55 degrees. In addition, it is contemplated that chamfer 32 may have an arcuate profile in a sagittal, coronal and/or transverse plane, and may include convex or concave curvature as required or desired for a particular application.

2. Progressive Peripheral Growth Between Implant Sizes

In addition to the asymmetry of each individual size/embodiment of tibial baseplate 12, described in detail above, the present disclosure also provides asymmetry in the way periphery 200 grows from one size to the next. Advantageously, this asymmetric peripheral growth accommodates observed growth trends in tibias T of differently-sized patients, while also preserving the optimal fit and coverage provided by baseplate 12, and offering the other advantages of designs in accordance with the present disclosure as described herein.

In symmetrical peripheral growth, a larger size of baseplate is a scaled-up version of a smaller size and vice-versa. In the present asymmetrical peripheral growth, by contrast, certain parameters of tibial baseplate 12 grow faster than others as the overall size of the baseplate gets larger (i.e., from smallest size 1/A through largest size 9/J). Thus, differently-sized components made in accordance with the present disclosure are not proportional to one another in all respects, in that a larger tibial prosthesis is not proportionally larger than a smaller tibial prosthesis in all aspects.

Referring now to FIG. 2B, periphery $200_X$ defines centroid $C_X$, which is medially biased with respect to home axis $A_H$ owing to medial surface area SAM being larger than lateral surface area SAL (as described in detail above). Posterior-medial distance $DMP_X$ extends from centroid $C_X$ toward the posterior-medial "corner" of periphery $200_X$ (i.e., toward posterior-medial corner arc 224, shown in FIG. 3A and described above) at an angle of 130 counter-clockwise degrees from home axis $A_H$. Similarly, posterior-lateral distance $DLP_X$ extends from centroid $C_X$ toward the posterior-lateral "corner" of periphery $200_X$ (i.e., toward posterior-lateral corner arc 214, shown in FIG. 3A and described above) at an angle of 120 clockwise degrees from home axis $A_H$. The posterior-lateral and posterior-medial corners are defined in a similar fashion as the anterior-lateral and anterior-medial corners, described in detail above. Moreover, while the asymmetric posterior-medial and posterior lateral growth among consecutive sizes is described below with respect to distances $DLP_X$, $DMP_X$, such growth occurs in the entire area occupied by the posterior-medial and posterior-lateral corners.

Figure 2C:
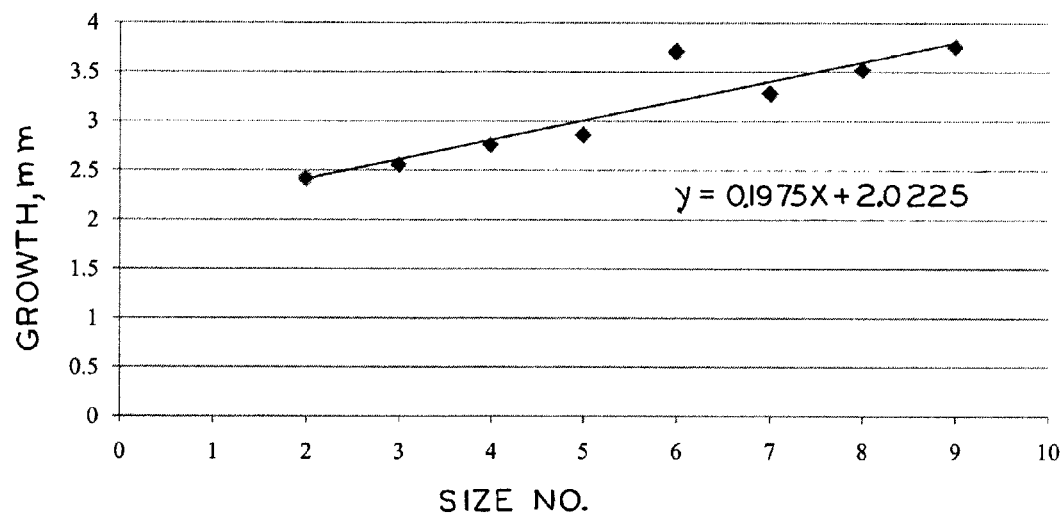
FIG. 2C is a graph illustrating the asymmetric growth of the posterior-medial compartment for the tibial baseplates shown in FIG. 2A.
Figure 2D:
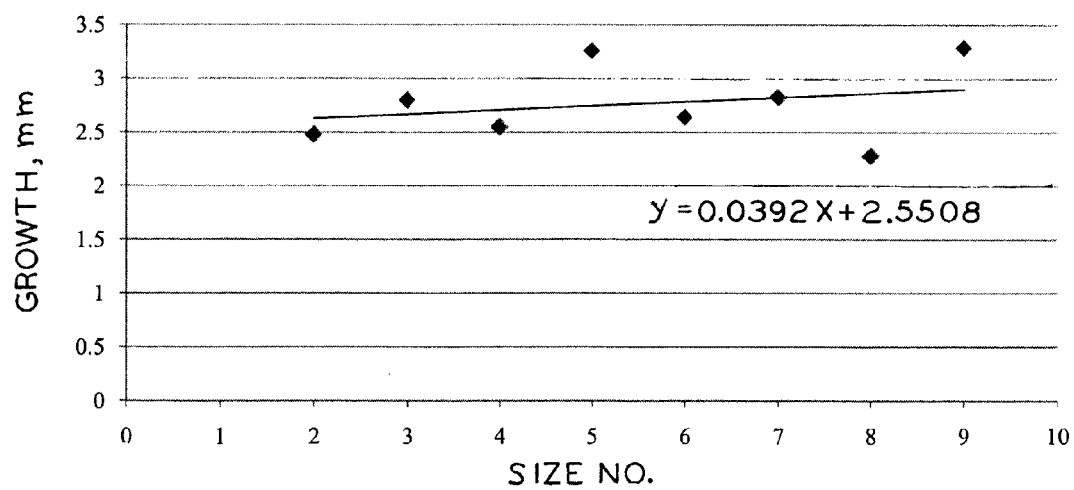
FIG. 2D is a graph illustrating the asymmetric growth of the posterior-lateral compartment for the tibial baseplates shown in FIG. 2A.

As illustrated in FIG. 2A and shown in Table 6 below, lateral- and medial-posterior distances $DLP_X$, $DMP_X$ do not grow linearly as smallest size 1/A progresses among consecutive sizes to eventually reach largest size 9/J. Rather, lateral- and medial-posterior distances $DLP_X$, $DMP_X$ exhibit an increase in the magnitude of growth as the sizes progress consecutively from size 1/A to size 9/J. This non-linear, asymmetric growth is illustrated in the graphs of FIGS. 2C and 2D and in Table 6 below.

TABLE 6

Growth of the Posterior-Medial and
Posterior-Lateral Corners of Baseplate Periphery
(FIGS. 2A and 2B)

| Size (X) | Growth in medial-posterior distance $DMP_x$ from centroid ($C_x$), compared to next-smaller size, mm | Growth in lateral-posterior distance ($DLP_x$) from centroid ($C_x$), compared to next-smaller size, mm |
|---|---|---|
| 1 | — | — |
| 2 | 2.42 | 2.48 |
| 3 | 2.56 | 2.8 |
| 4 | 2.76 | 2.55 |
| 5 | 2.86 | 3.26 |
| 6 | 3.71 | 2.64 |
| 7 | 3.28 | 2.83 |
| 8 | 3.52 | 2.28 |
| 9 | 3.76 | 3.29 |

In FIG. 2C, the amount of growth in $DMP_X$ is plotted against size no. X. As illustrated, the family of tibial baseplates 12 illustrated in FIG. 2A exhibit a steadily increasing growth in $DMP_X$, with nearly 20% average increase in growth from one size to the next consecutive size (as represented by the slope of the linear trend line having equation y=0.1975x+2.0225).

In FIG. 2D, the amount of growth in $DLP_X$ is plotted against size no. X, and illustrates a smaller, but still positive growth increase across baseplate sizes. More specifically, the family of tibial baseplates 12 illustrated in FIG. 2A exhibit a nearly 4% average increase in growth from one size to the next consecutive size (as represented by the slope of the linear trend line having equation y=0.0392x+2.5508).

As used herein, a "family" of prostheses refers to a set or kit of prostheses sharing common geometrical and/or performance characteristics. For example, the family of nine tibial baseplates whose peripheries $200_X$ are shown in FIG. 2A share a common asymmetry as described herein, such that each tibial baseplate is adapted to provide substantial tibial coverage, facilitate proper implant rotation and avoid impingement with various soft tissues of the knee. Typically, a family of prostheses includes a plurality of differently-sized components, with consecutively larger/smaller components sized to accommodate a variety of differently-sized bones. In the exemplary embodiments of the present disclosure, a size "1" or "A" prosthesis is the smallest prosthesis of the family, a size "9" or "J" prosthesis is the largest prosthesis of the family, and each of the intermediate sizes "2" or "B" through "8" or "H" are consecutively larger sizes.

Advantageously, in the family or kit of prosthesis peripheries shown in FIG. 2A, each tibial baseplate 12 (FIG. 1A) having periphery $200_X$ provides a close match to a particular subset of patient tibias T having a unique size and shape. Particular features of periphery $200_X$ have been designed with non-linear growth which is calculated to provide the closest possible fit for the largest number of particular natural geometries found in anatomic tibias T, as described in detail herein. This close fit allows for maximum coverage of the resected proximal tibial periphery $200_X$, by accommodating the non-linear changes which may occur across anatomic tibial periphery sizes. Lateral- and medial-posterior distances $DLP_X$, $DMP_X$ are exemplary non-linear growth parameters found in a family of tibial baseplates 12, and are reflective of non-linear growth in mediolateral extent $DML_X$ and anteroposterior extents $DAPM_X$ and $DAPL_X$ across the various sizes.

3. PCL Cutout Aligned with Home Axis and Associated Technique

In the illustrated embodiment, tibial plateau 18 includes PCL cutout 28 disposed between compartments 20, 22, as described above. PCL cutout leaves PCL attachment point $C_P$ accessible, thereby allowing the PCL to pass therethrough during and after implantation of tibial baseplate 12. Tibial bearing component 14 (FIG. 5) may similarly include cutout 30.

Thus, the illustrated embodiment of tibial prosthesis 10 is adapted for a cruciate retaining (CR) surgical procedure, in which the posterior cruciate ligament is not resected during implantation of tibial prosthesis 10. Further, as noted above, home axis $A_H$ includes reference to PCL attachment point $C_P$ when tibial baseplate 12 is mounted upon tibia T. In order to facilitate alignment of home axis $A_H$ with respect to tibial baseplate 12 and tibia T, alignment indicia 70A, 70P (FIGS. 4A and 4B) may be marked on proximal surface 34 and/or peripheral wall 25. When tibial baseplate 12 is implanted (as described below), anterior alignment indicia 70A (FIGS. 4A and 4B) is aligned with anterior point $C_A$ at the "medial third" of the anterior tibial tubercle T, and posterior alignment indicia 70P is aligned with the natural PCL attachment point $C_p$ of tibia T.

However, it is contemplated that a prosthesis in accordance with the present disclosure may be made for a design in which the posterior cruciate ligament is resected during surgery, such as "posterior stabilized" (PS) or "ultra congruent" (UC) designs. The PS and UC designs may exclude PCL cutout 30 in bearing component 14, thereby obviating the need for PCL cutout 28 in tibial baseplate 12. Continuous material may instead occupy cutout 28 (as schematically shown in FIG. 3D). Moreover, it is contemplated that PCL cutouts 28, 30 may have any shape and/or size within the scope of the present disclosure. For example, PCL cutouts 28, 30 may be asymmetrical with respect to an anteroposterior axis. For purposes of the present disclosure "bisecting" an asymmetric PCL cutout with an anteroposterior axis refers to dividing such cutout into two equal areas for a given anteroposterior section of the anteroposterior axis

4. Tibial Bearing Component and Deep Flexion Enablement

Turning again to FIG. 1A, tibial bearing component 14 includes lateral portion 39, medial portion 41, inferior surface 36 adapted to couple to tibial baseplate 12, and superior surface 38 adapted to articulate with condyles of a femoral component (such as femoral component 60 shown in FIG. 8 and described in detail below). Superior surface 38 includes lateral articular surface 40 in lateral portion 39 and medial articular surface 42 in medial portion 41, with eminence 44 (FIG. 5) disposed between articular surfaces 40, 42. Referring to FIG. 5, eminence 44 generally corresponds in shape and size with a natural tibial eminence of tibia T prior to resection.

Referring now to FIG. 1A, tibial plateau 18 of tibial baseplate 12 further includes a distal or bone contacting surface 35 and an opposing proximal or superior surface 34, with superior surface 34 having raised perimeter 24 and locking mechanism 26 formed between lateral and medial compartments 20, 22. Raised perimeter 24 and locking mechanism 26 cooperate to retain tibial bearing component 14 upon tibial baseplate 12, as described in detail below. Exemplary baseplate locking mechanisms are described in U.S. provisional patent application Ser. Nos. 61/367,374 and 61/367,375, both entitled TIBIAL PROSTHESIS and both incorporated by reference as stated above.

Inferior surface 36 of tibial bearing component 14 includes recess 46 at the periphery thereof and a tibial bearing locking mechanism (not shown) disposed between lateral and medial articular surfaces 40, 42. Exemplary bearing component locking mechanisms are disclosed in U.S. provisional patent application Ser. Nos. 61/367,374 and 61/367,375, both entitled TIBIAL PROSTHESIS. Recess 46 is sized and positioned to correspond with raised perimeter 24 of tibial plateau 18, and the tibial bearing locking mechanism cooperates with locking mechanism 26 of tibial plateau 18 to fix tibial bearing component 14 to tibial baseplate 12 in a desired position and orientation as described in detail below. However, it is contemplated that tibial bearing component 14 may be affixed to baseplate 12 by any suitable mechanism or method within the scope of the present disclosure, such as by adhesive, dovetail tongue/groove arrangements, snap-action mechanisms, and the like.

As best seen in FIGS. 1B, 5 and 8, the outer periphery of tibial bearing component 14 generally corresponds with the outer periphery of tibial plateau 18, except for the posteromedial extent of plateau 18 as compared with tibial bearing component 14. The anterolateral "corner" of tibial bearing component 14 defines radius $R_3$ (FIG. 5) having a generally common center with radius R2L of baseplate 12 in a transverse plane, i.e., radii R2L and $R_3$ are substantially coincident in a plan view. Similarly, the anteromedial "corner" of tibial bearing component 14 defines radius $R_4$ having a generally common center with radius R1R of baseplate 12 in a transverse plane, i.e., radii R1R and $R_4$ are substantially coincident in a plan view.

$R_3$ defines a slightly smaller radial length as compared to R2L, and $R_4$ defines a slightly smaller radial length as compared to R1R, such that the anterior portion of perimeter wall 54 of tibial bearing component 14 is set back from the anterior portion of peripheral wall 25 (i.e., from anterior edge 202 and adjacent arcs, as described above) of tibial baseplate 12. As with the above-described comparison between radii R2L and R1R, anteromedial radius $R_4$ is substantially larger than anterolateral radius $R_3$.

Given that medial portion 41 of tibial bearing component 14 has a lesser anteroposterior extent compared to medial compartment 22 of tibial plateau 18, medial portion 41 must be biased anteriorly in order for the anterior-medial "corners" of tibial bearing component 14 and tibial plateau 18 to coincide as shown in FIG. 5. In view of this anterior bias, it may be said that tibial bearing component 14 is asymmetrically oriented upon tibial plateau 18. More particularly, although lateral articular surface 40 is generally centered with respect to lateral compartment 20 of tibial plateau 18, medial articular surface 42 is anteriorly biased with respect to medial compartment 22 of tibial plateau 18 in order to leave chamfer 32 exposed at the posterior-lateral corner. This asymmetric mounting of tibial bearing component 14 upon tibial plateau 18 ensures a desired articular interaction between tibial prosthesis 10 and femoral component 60, as described in detail below.

Tibial plateau 18 of tibial baseplate 12 deviates from the periphery of tibial bearing component 14 in the posteromedial portion of each component, leaving medial portion 41 incongruent with medial compartment 22 of tibial baseplate 12. More particularly, tibial plateau 18 extends posteromedially to substantially cover the proximal resected surface of tibia T, as shown in FIG. 5 and described in above, while tibial bearing component 14 does not extend posteromedially beyond the superior terminus of chamfer 32 (i.e., tibial bearing component 14 does not "overhang" chamfer 32). In addition, tibial bearing component 14 includes chamfer 50 formed in peripheral wall 54, with chamfer 50 having a profile and geometrical arrangement corresponding with chamfer 32 of tibial plateau 18. More particularly, when tibial bearing component 14 is assembled to tibial baseplate 12 as shown in FIGS. 1B and 8, the anterior orientation or "bias" of the medial portion of tibial bearing component 14 (as described above) aligns chamfers 32, 50, which in turn cooperate to create a substantially continuous chamfer extending from tibia T to medial articular surface 42. Referring to FIG. 8, chamfers 32, 50 further cooperate to define void 52 formed between femur F and tibial plateau 18 when tibial prosthesis 10 is in a deep flexion orientation. In the illustrated embodiment of FIG. 8, the deep flexion orientation is defined by angle β between anatomic tibia axis $A_T$ and anatomic femoral axis $A_F$ of up to about 25 degrees to about 40 degrees, for example (i.e., about 140 degrees to 155 degrees of flexion or more).

Advantageously, void 52 cooperates with the "pulled back" or incongruent posterior medial edge 206 and posterior medial corner 224, as compared to a typical tibial periphery (described above), to allow the deep flexion orientation to be achieved without impingement of femoral component 60 and/or femur F upon tibial plateau 18 and/or tibial bearing component 14. Soft tissues in the region of void 52 are therefore also accommodated with little or no impingement on the surrounding components.

In addition, the relatively large size of tibial plateau 18 (covering a large proportion of the resected proximal surface of tibia T) also allows tibial bearing component 14 to be relatively large, so that tibial bearing component 14 provides sufficient non-articular surface area at chamfers 32, 50 and around the periphery of lateral and medial articular surfaces 40, 42 to allow relatively large-radius, rounded transitions between articular surfaces 40, 42 and peripheral wall 54 of tibial bearing component 14. These gradual, large-radius transitions prevent undue friction between tibial prosthesis 10 and any surrounding soft tissues which may remain in place after implantation of the prosthesis, such as the iliotibial (IT) band.

In certain ranges of prosthesis articulation, for example, the human iliotibial (IT) band may touch the anterolateral "corner", i.e., the portion of tibial bearing component 14 having radius $R_3$. Because the anterolateral extent of tibial bearing component 14 follows the anterolateral extent of tibial plateau 18 (as described above), the transition between lateral articular surface 40 and peripheral wall 54 at the point of contact between an IT band and tibial bearing component 14 can have a relatively large convex portion while still leaving sufficient concave space for articular surface 40. This large convex portion results in a large contact area if the IT band does contact tibial bearing component 14, which in turn results in relatively low pressures on the IT band. Further, the anterolateral "pull back" or incongruence between the anterior-lateral corner arc 210 of periphery 200 and a typical tibial periphery, described in detail above, allows the corresponding anterior-lateral corner of bearing component 14 to maintain separation from the IT band through a wide range of flexion, and low contact pressures where contact does occur.

However, to any such contact between the IT band and tibial bearing component 14 may be avoided or minimized by designing periphery 200 such that anterior-lateral corner arc 210 and/or lateral edge arc 212 is brought away from the expected periphery of a typical tibia T (as calculated from anatomical data, described above). This extra spacing designed into periphery 200 provides extra clearance for the iliotibial band. In addition, this extra clearance assures that the substantial proportion of prospective patients lacking Gerdy's tubercle, which is an eminence located at the anterior-lateral portion of tibia T, will not experience any "overhang" of tibial plateau 18 beyond the anatomic periphery of resected tibia T.

Thus, generally speaking, tibial prosthesis 10 can be considered "soft tissue friendly" because the edges of tibial bearing component 14 and tibial plateau 18, including chamfers 32, 50, are smooth and rounded, so that any soft tissue coming into contact with these edges will be less likely to chafe or abrade.

Advantageously, the relatively large inferior/distal surface area of tibial plateau 18 facilitates a large amount of bone ingrowth where bone ingrowth material is provided in tibial baseplate 12. For example, baseplate 12 may also be constructed of, or may be coated with, a highly porous biomaterial. A highly porous biomaterial is useful as a bone substitute and as cell and tissue receptive material. A highly porous biomaterial may have a porosity as low as 55%, 65%, or 75% or as high as 80%, 85%, or 90%. An example of such a material is produced using Trabecular Metal™ Technology generally available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 to Kaplan, the entire disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that growth of cancellous bone through the porous tantalum structure is uninhibited. The porous tantalum may include up to 75%, 85%, or more void space therein. Thus, porous tantalum is a lightweight, strong porous structure which is substantially uniform and consistent in composition, and closely resembles the structure of natural cancellous bone, thereby providing a matrix into which cancellous bone may grow to provide fixation of implant [#] to the patient's bone.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization.

5. Trial Tibial Components

Tibial prosthesis 10 may be provided in a variety of sizes and configurations to accommodate different bone sizes and geometries. The choice of one particular size may be planned preoperatively such as through preoperative imaging and other planning procedures. Alternatively, an implant size may be chosen, or a previous size choice modified, intraoperatively. To facilitate proper intraoperative selection of a particular size for tibial prosthesis 10 from among the family of sizes shown in FIG. 2A, and to promote proper orientation of the chosen prosthesis 10, tibial prosthesis 10 may be part of a kit including one or more template or "sizing" components.

Figure 6:
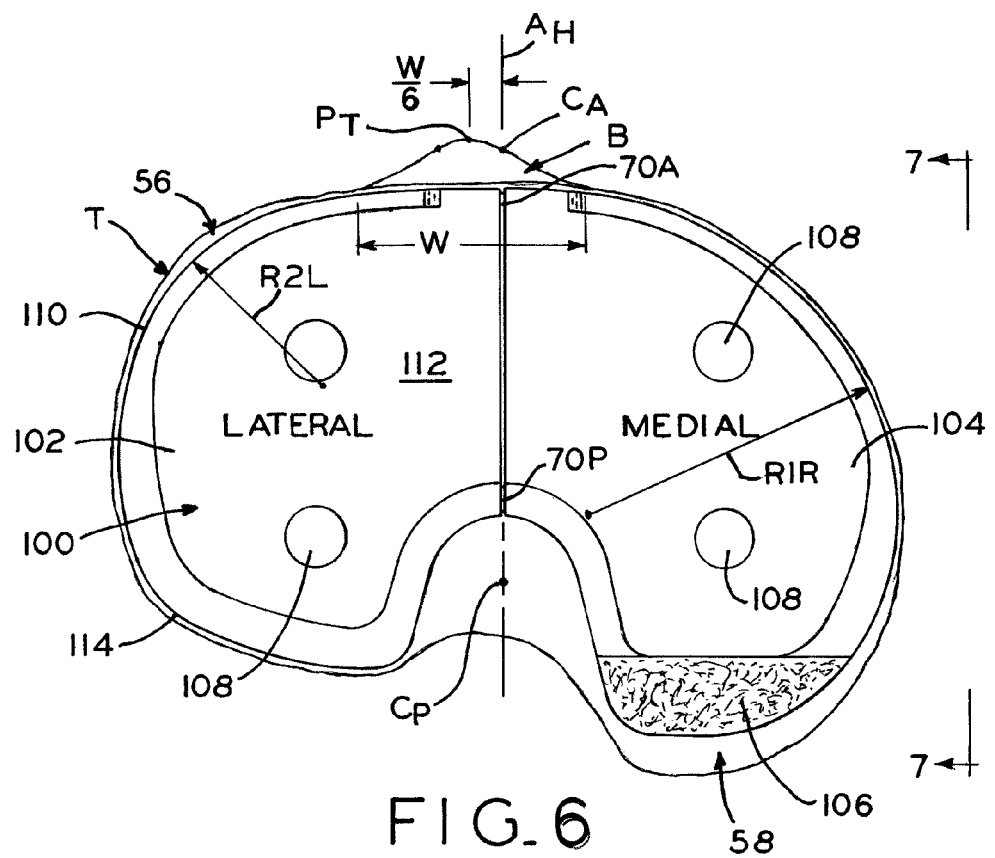
FIG. 6 is a top plan view of a resected proximal tibial surface with a properly sized tibial trial component thereon.
Figure 7:
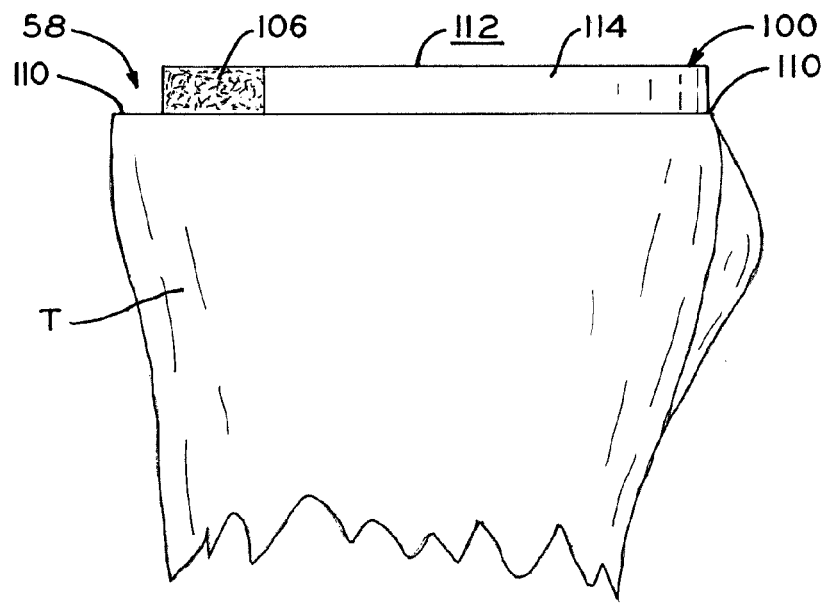
FIG. 7 is a side, elevation view of the tibia and trial component shown in FIG. 6.

Referring now to FIGS. 6 and 7, trial prosthesis 100 may be temporarily coupled to tibia T for intraoperative sizing evaluation of tibial prosthesis 10 and initial steps in the implantation of tibial prosthesis 10. Trial prosthesis 100 is one of a set of trial prostheses provided as a kit, with each trial prosthesis having a different size and geometrical configuration. Each trial prosthesis in the set of trial prostheses corresponds to a permanent prosthesis 10, such as sizes 1/A-9/J of tibial baseplate 12 as described above.

For example, as shown in FIG. 6, trial prosthesis 100 defines superior surface 112 generally corresponding in size and shape to proximal surface 34 of tibial plateau 18, and including lateral portion 102 and medial portion 104. Superior surface 112 is asymmetrical about home axis $A_H$, with lateral portion 102 having a generally shorter overall anteroposterior extent as compared to medial portion 104 (which includes void indicator 106, discussed below). In addition, the anterolateral "corner" of lateral portion 102 defines radius R2L, which is identical to radius R2L of tibial plateau 18, while the anteromedial "corner" of medial portion 104 defines radius R1R, which is identical to radius R1R of tibial plateau 18 and greater than radius R2L.

Moreover, perimeter wall 114 of trial prosthesis 100 is substantially identical to peripheral wall 25 of tibial plateau 18, and therefore defines periphery 200 with the same features and shapes of perimeter 200 described above with respect to tibial plateau 18. Thus, trial prosthesis 100 is asymmetrical about home axis $A_H$ in a similar manner to tibial plateau 18 of tibial baseplate 12, with the nature of this asymmetry changing across the various other sizes of tibial prosthesis provided in the kit including trial prosthesis 100.

In an alternative embodiment, a trial prosthesis may be provided which extends completely to the posterior-medial edge of the natural tibial resection periphery. Thus, such a trial would substantially completely cover the resected tibial surface, thereby aiding in determination of a proper rotational orientation of the trial (and, therefore, of the final tibial baseplate 12). In this alternative embodiment, the trial prosthesis lacks the posterior-medial "pull back" of tibial plateau 18, described above.

Trial prosthesis 100 includes void indicator 106 disposed at the posterior portion of medial portion 104, consuming a given posteromedial area of superior surface 34 and peripheral wall 25. Void indicator 106 indicates where void 52 (discussed above) will be located with respect to tibia T after implantation of tibial prosthesis 10. Void indicator 106 facilitates proper rotational and spatial orientation of trial prosthesis 100 on the resected proximal surface of tibia T by allowing a surgeon to visually match tibial bearing component 14 with trial prosthesis 100, as described in detail below. In the illustrated embodiment, void indicator 106 is an area of visual and/or tactile contrast with the remainder of tibial plateau 18. This contrast may include, for example, a contrasting color, texture, surface finish, or the like, or may be formed by a geometric discrepancy such as a step or lip, for example.

Referring specifically to FIG. 6, trial prosthesis 100 further includes a plurality of peg hole locators 108 corresponding to the proper location for peg holes in tibia T to receive pegs (not shown) extending inferiorly from tibial plateau 18 of tibial baseplate 12. Advantageously, peg hole locators 108 allow a surgeon to demarcate the proper center for peg holes in tibia T once the proper size and orientation for trial prosthesis 100 has been found, as discussed in detail below. Alternatively, peg hole locators 108 may be used as drill guides to drill appropriately positioned peg holes while trial prosthesis is still positioned on tibia T.

6. Tibial Prosthesis Implantation

In use, a surgeon first performs a resection of tibia T using conventional procedures and tools, as are well-known in the art. In an exemplary embodiment, a surgeon will resect the proximal tibia to leave a planar surface prepared for receipt of a tibial baseplate. This planar surface may define a tibial slope, which is chosen by the surgeon. For example, the surgeon may wish to perform a resection resulting in positive tibial slope in which the resected tibial surface slopes proximally from posterior to anterior (i.e., the resected surface runs "uphill" from posterior to anterior). Alternatively, the surgeon may instead opt for negative tibial slope in which the resected tibial surface slopes distally from posterior to anterior (i.e., the resected surface runs "downhill" from posterior to anterior). Varus or valgus slopes may also be employed, in which the resected surface slopes proximally or distally from medial to lateral. The choice of a tibial and/or varus/valgus slope, and the amount or angle of such slopes, may depend upon a variety of factors including correction of deformities, mimicry of the native/preoperative tibial slope, and the like.

In an exemplary embodiment, keel 16 (FIG. 4B) defines a 5-degree, anteriorly-extending angle with respect to bone-contacting surface 35 of tibial plateau 18. Tibial baseplate 12 is appropriate for use with a positive tibial slope of as little as zero degrees and as much as 9 degrees, and with a varus or valgus slope of up to 3 degrees. However, it is contemplated that a tibial baseplate made in accordance with the present disclosure may be used with any combination of tibial and/or varus/valgus slopes, such as by changing the angular configuration of the keel with respect to the bone-contacting surface.

With a properly resected proximal tibial surface, the surgeon selects trial prosthesis 100 from a kit of trial prostheses, with each prosthesis in the kit having a different size and geometrical configuration (as discussed above). Trial prosthesis 100 is overlaid on the resected surface of tibia T. If trial prosthesis 100 is appropriately sized, a small buffer zone 110 of exposed bone of resected tibia T will be visible around the periphery of trial prosthesis 100. Buffer 110 is large enough to allow a surgeon to rotate and/or reposition trial prosthesis 100 within a small range, thereby offering the surgeon some flexibility in the final positioning and kinematic profile of tibial prosthesis 10. However, buffer 110 is small enough to prevent trial prosthesis 100 from being rotated or moved to an improper location or orientation, or from being implanted in such as way as to produce excessive overhang of the edge of trial prosthesis 100 past the periphery of the resected tibial surface. In one exemplary embodiment, for example, trial prosthesis may be rotated from a centered orientation by up to +/−5 degrees (i.e., in either direction), though it is contemplated that such rotation may be as much as +/−10 degrees or +/−15 degrees.

To aid in rotational orientation, trial prosthesis may include anterior and posterior alignment indicia 70A, 70P, which are the same marks in the same location as indicia 70A, 70P provided on tibial plateau 18 as described above. The surgeon can align indicia 70A with anterior point $C_A$ and indicia 70P with PCL attachment point $C_P$, in similar fashion as described above, to ensure the anatomical and component home axes $A_H$ are properly aligned. Alternatively, a surgeon may use indicia 70A, 70P to indicate a desired deviance from alignment with home axis $A_H$. As noted above, deviation of up to 5 degrees is envisioned with the exemplary embodiments described herein. A surgeon may choose to orient indicia 70A, 70P to another tibial landmark, such as the middle of the patella or the medial end of tibial tubercle B.

Thus, the large coverage of trial prosthesis 100 (and, concomitantly, of tibial plateau 18) ensures that tibial baseplate 12 will be properly positioned and oriented on tibia T upon implantation, thereby ensuring proper kinematic interaction between tibial prosthesis 10 and femoral component 60. If buffer zone 110 is either nonexistent or too large, another trial prosthesis 100 is selected from the kit and compared in a similar fashion. This process is repeated iteratively until the surgeon has a proper fit, such as the fit illustrated in FIGS. 6 and 7 between trial prosthesis 100 and tibia T.

With the proper size for trial prosthesis 100 selected and its orientation on tibia T settled, trial prosthesis 100 is secured to tibia T, such as by pins, screws, temporary adhesive, or any other conventional attachment methods. Once trial prosthesis is so secured, other trial components, such as trial femoral components and trial tibial bearing components (not shown) may be positioned and used to articulate the leg through a range of motion to ensure a desired kinematic profile. During such articulation, void indicator 106 indicates to the surgeon that any impingement of femoral component 60 and/or femur F upon trial prosthesis 100 at void indicator 106 will not occur when tibial prosthesis 10 is implanted. Once the surgeon is satisfied with the location, orientation and kinematic profile of trial prosthesis 100, peg hole locators 108 may be used to demarcate the appropriate location of peg holes in tibia T for tibial baseplate 12. Such peg holes may be drilled in tibia T with trial prosthesis 100 attached, or trial prosthesis 100 may be removed prior to drilling the holes.

With tibia T prepared for receipt of tibial prosthesis 10, tibial baseplate 12 may be provided by the surgeon (such as from a kit or surgical inventory), and is implanted on tibia T, with pegs fitting into holes previously identified and demarcated using peg hole locators 108 of trial prosthesis 100. Tibial baseplate 12 is selected from the family of tibial baseplates illustrated in FIG. 2A to correspond with the trial component 100 chosen, which ensures that tibial plateau 18 will cover a large proportion of the resected proximal surface of tibia T, as trial prosthesis 100 did prior to removal. Tibial baseplate is affixed to tibia T by any suitable method, such as by keel 16 (FIG. 4B), adhesive, bone-ingrowth material, and the like.

With tibial baseplate 12 installed, tibial bearing component 14 may be coupled with tibial baseplate 12 to complete tibial prosthesis 10. However, once attached, tibial bearing component 14 does not fully cover tibial plateau 18 of tibial baseplate 12. Rather, tibial bearing component 14 leaves a posteromedial portion of tibial baseplate 12 uncovered to create void 52 (as shown in FIG. 8 and discussed above). Thus, a surgeon may wish to verify that this anterior-biased, "asymmetrical" orientation of medial articular surface 42 is proper prior to permanent affixation of tibial bearing component 14 to tibial baseplate 12.

To accomplish such verification, tibial bearing component 14 is placed side-by-side with trial prosthesis 100, with inferior surface 36 of tibial bearing component 14 in contact with superior surface 112 of trial prosthesis 100. Tibial bearing component 14 will substantially cover superior surface 112, but will not cover void indicator 106. Put another way, peripheral wall 54 of tibial bearing component 14 will trace perimeter wall 114 of tibial trial prosthesis 100, excluding the posteromedial area defined by void indicator 106. If inferior surface 36 of tibial bearing component 14 is a match with superior surface 112 of trial prosthesis 100 except for void indicator 106 (which is left uncovered by tibial bearing component 14), then tibial bearing component 14 is the proper size component and may be confidently installed upon tibial plateau 18 of tibial baseplate 12.

Tibial baseplate 12 may then be implanted upon the proximal surface of tibia T in accordance with accepted surgical procedures. Exemplary surgical procedures and associated surgical instruments are disclosed in "Zimmer LPS-Flex Fixed Bearing Knee, Surgical Technique," "NEXGEN COMPLETE KNEE SOLUTION, Surgical Technique for the CR-Flex Fixed Bearing Knee" and "Zimmer NexGen Complete Knee Solution Extramedullary/Intramedullary Tibial Resector, Surgical Technique" (collectively, the "Zimmer Surgical Techniques"), copies of which are submitted on even date herewith, the entire disclosures of which are hereby expressly incorporated by reference herein.

When the surgeon is satisfied that tibial bearing component 14 is properly matched and fitted to the installed tibial baseplate 12, bearing component 14 is secured using locking mechanism 26 and the corresponding tibial bearing locking mechanism an appropriate instrumentation (not shown). Proper location and rotational orientation of tibial bearing component 14 upon tibial plateau 18 is ensured by raised perimeter 24 cooperating with recess 46, and locking mechanism 26 cooperating with the corresponding tibial bearing locking mechanism (not shown). Such proper orientation results in medial articular surface 42 being generally anteriorly disposed with respect to medial compartment 22 of tibial plateau 18.

Femoral component 60 may be affixed to a distal end of femur F, if appropriate, using any conventional methods and/or components. Exemplary surgical procedures and instruments for such affixation are disclosed in the Zimmer Surgical Techniques, incorporated by reference above. Femur F and tibia T may then be articulated with respect to one another to ensure that neither femur F nor femoral component 60 impinges upon tibial baseplate 12 and/or tibial bearing component 14 in deep flexion, such as at a flexion angle $\beta$ of 155° as shown in FIG. 8. When the surgeon is satisfied with the location, orientation and kinematic profile of tibial prosthesis 10, the knee replacement surgery is completed in accordance with conventional procedures.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A tibial prosthesis comprising an asymmetric prosthesis periphery, said prosthesis comprising:
   a distal surface;
   a proximal surface generally opposite said distal surface, said proximal surface having a lateral compartment and a medial compartment; and
   a peripheral wall extending between said distal and said proximal surface, said peripheral wall defining:
   an anterior edge;
   a lateral posterior edge generally opposite said anterior edge and forming a posterior boundary of said lateral compartment;
   a medial posterior edge generally opposite said anterior edge and forming a posterior boundary of said medial compartment;

a lateral periphery extending from said anterior edge to said lateral posterior edge, said lateral periphery defining a plurality of adjacent lateral arcs, an adjacent pair of said plurality of adjacent lateral arcs defining a first lateral radius and a second lateral radius, respectively, said first lateral radius larger than said second lateral radius by at least 100%, whereby said lateral periphery is relatively boxy; and a medial periphery extending from said anterior edge to said medial posterior edge, said medial periphery defining a plurality of adjacent medial arcs, an adjacent pair of said plurality of adjacent medial arcs defining a first medial radius and a second medial radius, respectively, said first medial radius larger than said second medial radius by less than 75%, whereby said medial periphery is generally rounded, wherein said tibial prosthesis comprises a tibial baseplate and a tibial bearing component, said tibial baseplate including an anterior-lateral corner defining an anterior-lateral corner radius having a first radial center, and an anterior-medial corner defining an anterior-medial corner radius having a second radial center, said tibial bearing component comprising:
  a lateral portion defining an anterior-lateral bearing corner defining a third radius having a third radial center, said third radial center substantially coincident with said first radial center in a transverse plane when said tibial bearing component is mounted to said tibial baseplate, said third radius smaller than said anterior-lateral corner radius; and
  a medial portion defining an anterior-medial bearing corner defining a fourth radius having a fourth radial center, said fourth radial center substantially coincident with said second radial center in the transverse plane when said tibial bearing component is mounted to said tibial baseplate, said fourth radius smaller than said anterior-medial corner radius, said fourth radius substantially larger than said third radius,
  wherein said lateral periphery is asymmetric with respect to said medial periphery about an anteroposterior axis.

2. The tibial prosthesis of claim 1, wherein said lateral periphery comprises:
  a lateral edge defining a substantially perpendicular tangent with respect to said anterior edge, said lateral edge defining a lateral edge radius,
  an anterior-lateral corner traversing an angular sweep between said anterior edge and said lateral edge,
  said anterior-lateral corner defining an anterior-lateral corner radius, said lateral edge radius larger than said anterior-lateral corner radius by at least 42%.

3. The tibial prosthesis of claim 2, wherein said lateral edge radius is larger than said anterior-lateral corner radius by up to 142%.

4. The tibial prosthesis of claim 1, wherein said lateral periphery comprises:
  a lateral edge defining a substantially perpendicular tangent with respect to said anterior edge, said lateral edge defining a lateral edge radius,
  a posterior-lateral corner traversing an angular sweep between said lateral posterior edge and said lateral edge,
  said posterior-lateral corner defining a posterior-lateral corner radius, said lateral edge radius larger than said posterior-lateral corner radius by at least 198%.

5. The tibial prosthesis of claim 4, wherein said lateral edge radius is larger than said posterior-lateral corner radius by up to 324%.

6. The tibial prosthesis of claim 1, wherein said plurality of adjacent lateral arcs each define a respective lateral radius value, each respective radius value different from all of the other radius values.

7. The tibial prosthesis of claim 1, wherein at least one of said anterior edge, said lateral posterior edge and said medial posterior edge is planar.

8. The tibial prosthesis of claim 1, wherein said lateral periphery comprises:
  a lateral edge defining a substantially perpendicular tangent with respect to said anterior edge;
  an anterior-lateral corner traversing an angular sweep between said anterior edge and said lateral edge; and
  an arcuate anterior section between said anterior edge and said anterior-lateral corner, said arcuate anterior section defining one of said plurality of adjacent lateral arcs.

9. The tibial prosthesis of claim 1, wherein said plurality of adjacent lateral arcs are greater in number as compared to said plurality of adjacent medial arcs.

10. The tibial prosthesis of claim 1, wherein said plurality of adjacent lateral arcs comprises at least five adjacent lateral arcs.

11. The tibial prosthesis of claim 1, wherein said plurality of adjacent medial arcs comprises up to three adjacent lateral arcs.

12. The tibial prosthesis of claim 1, wherein said anterior-medial corner radius is larger than said anterior-lateral corner radius by at least 48%.

13. The tibial prosthesis of claim 1, wherein said anterior-medial corner radius is larger than said anterior-lateral corner radius by up to 149%.

14. The tibial prosthesis of claim 1, wherein:
  said medial compartment defines a medial anteroposterior extent extending from said anterior edge of said peripheral wall to said medial posterior edge, and
  said lateral compartment defines a lateral anteroposterior extent extending from said anterior edge of said peripheral wall to said lateral posterior edge,
  said medial anteroposterior extent larger than said lateral anteroposterior extent.

15. The tibial prosthesis of claim 1, wherein said anteroposterior axis is aligned with a home axis when said tibial prosthesis is mounted to a tibia, said home axis defined as a line extending from
  a posterior point at a geometric center of an attachment area between a posterior cruciate ligament and the tibia, to
  an anterior point disposed on an anterior tubercle of the tibia, the tubercle having a tubercle width W, said anterior point disposed on the tubercle at a location medially spaced from a midpoint of the tubercle by an amount equal to W/6.

16. The tibial prosthesis of claim 1, wherein:
  said tibial prosthesis includes a PCL cutout area generally opposite said anterior edge and between said lateral periphery and said medial periphery, and
  said anteroposterior axis bisects said anterior edge and bisects said PCL cutout area.

17. The tibial prosthesis of claim 16, wherein:
  said medial periphery cooperates with said anteroposterior axis to bound a medial surface area,
  said lateral periphery cooperates with said anteroposterior axis to bound a lateral surface area, and
  said medial surface area is larger than said lateral surface area.

18. The tibial prosthesis of claim 1, wherein said tibial prosthesis is sized and shaped to cover between about 60% and about 90% of a resected proximal surface of a tibia to create a buffer zone on all sides between a perimeter of a surface of the tibia and the peripheral wall.

19. A tibial prosthesis comprising an asymmetric prosthesis periphery, said prosthesis comprising:
a distal surface;
a proximal surface generally opposite said distal surface; and
a peripheral wall extending between said distal and said proximal surface, said peripheral wall defining:
an anterior edge;
a lateral periphery including:
a lateral edge defining a substantially perpendicular tangent with respect to said anterior edge,
an anterior-lateral corner traversing an angular sweep between said anterior edge and said lateral edge to define a boxy corner periphery having an anterior-lateral corner edge length, and
a posterior-lateral corner extending away from said lateral edge and said anterior-lateral corner; and
a medial periphery including:
a medial edge defining a substantially perpendicular tangent with respect to said anterior edge,
an anterior-medial corner traversing an angular sweep between said anterior edge and said medial edge to define a rounded corner periphery having an anterior-medial corner edge length that is longer than the anterior-lateral corner edge length, in which the angular sweep between said anterior edge and said medial edge is similar to the angular sweep between said anterior edge and said lateral edge, and
a posterior-medial corner extending away from said medial edge and said anterior-medial corner,
wherein said tibial prosthesis comprises a tibial baseplate, said distal surface comprising a bone contacting surface and said proximal surface comprising a tibial bearing engagement surface,
wherein:
said anterior-lateral corner comprises an anterior-lateral corner arc defining an anterior-lateral corner radius having a first radius center, and
said anterior-medial corner comprises an anterior-medial corner arc defining an anterior-medial corner radius having a second radius center, said tibial baseplate in combination with a tibial bearing component mountable to said tibial baseplate,
said tibial bearing component comprising:
a lateral portion defining an anterior-lateral bearing corner defining a third radius having a third radius center, said third radius center substantially coincident with said first radius center in a transverse plane when said tibial bearing component is mounted to said tibial baseplate, said third radius smaller than said anterior-lateral corner radius; and
a medial portion defining an anterior-medial bearing corner defining a fourth radius having a fourth radius center, said fourth radius center substantially coincident with said second radius center in the transverse plane when said tibial bearing component is mounted to said tibial baseplate, said fourth radius smaller than said anterior-medial corner radius, said fourth radius substantially larger than said third radius,
wherein said lateral periphery is asymmetric with respect to said medial periphery about an antero-posterior axis.

20. The tibial prosthesis of claim 19, wherein:
said lateral edge comprises a lateral edge arc defining a lateral edge radius, and
said lateral edge radius larger than said anterior-lateral corner radius by at least 42%.

21. The tibial prosthesis of claim 20, wherein said lateral edge radius is larger than said anterior-lateral corner radius by up to 142%.

22. The tibial prosthesis of claim 19, wherein:
said lateral edge comprises a lateral edge arc defining a lateral edge radius, said posterior-lateral corner comprises a posterior-lateral corner arc defining a posterior-lateral corner radius, and
said lateral edge radius larger than said posterior-lateral corner radius by at least 198%.

23. The tibial prosthesis of claim 22, wherein said lateral edge radius is larger than said posterior-lateral corner radius by up to 324%.

24. The tibial prosthesis of claim 19, wherein:
said medial edge comprises a medial edge arc defining a medial edge radius,
said anterior-medial corner comprises an anterior-medial corner arc defining an anterior-medial corner radius, and
said medial edge radius larger than said anterior-medial corner radius by up to 74%.

25. The tibial prosthesis of claim 19, wherein:
said medial edge comprises a medial edge arc defining a medial edge radius,
said posterior-medial corner comprises a posterior-medial corner arc defining a posterior-medial corner radius, and
said medial edge radius larger than said posterior-medial corner radius by up to 61%.

26. The tibial prosthesis of claim 19, wherein:
said anterior-medial corner radius is different from said anterior-lateral corner radius.

27. The tibial prosthesis of claim 19, wherein said lateral periphery defines an arcuate anterior section between said anterior edge and said anterior-lateral corner.

28. The tibial prosthesis of claim 19, wherein:
said lateral periphery defines a plurality of adjacent lateral arcs,
said medial periphery defines a plurality of adjacent medial arcs,
said plurality of adjacent lateral arcs greater in number as compared to said plurality of adjacent medial arcs.

29. The tibial prosthesis of claim 28, wherein said plurality of adjacent lateral arcs comprises at least five adjacent lateral arcs.

30. The tibial prosthesis of claim 28, wherein said plurality of adjacent medial arcs comprises up to three adjacent lateral arcs.

31. The tibial prosthesis of claim 19, wherein:
said anterior-medial corner radius is larger than said anterior-lateral corner radius.

32. The tibial prosthesis of claim 19, wherein said tibial baseplate is sized and shaped to cover between about 60% and about 90% of a resected proximal surface of a tibia to create a buffer zone on all sides between a perimeter of a surface of the tibia and the peripheral wall.

33. The tibial prosthesis of claim 19, wherein said antero-posterior axis is aligned with a home axis when said tibial prosthesis is mounted to a tibia, said home axis defined as a line extending from a posterior point at a geometric center of an attachment area between a posterior cruciate ligament and the tibia, to an anterior point disposed on an anterior tubercle of the tibia, the tubercle having a tubercle width W, said anterior point disposed on the tubercle at a location medially spaced from a midpoint of the tubercle by an amount equal to W/6.

34. The tibial prosthesis of claim 19, wherein:
said tibial prosthesis includes a PCL cutout area generally opposite said anterior edge and between said lateral periphery and said medial periphery, and
said anteroposterior axis bisects said anterior edge and bisects said PCL cutout area.

35. The tibial prosthesis of claim 19, wherein:
said medial periphery cooperates with said anteroposterior axis to bound a medial surface area,
said lateral periphery cooperates with said anteroposterior axis to bound a lateral surface area, and
said medial surface area is larger than said lateral surface area.

36. The tibial prosthesis of claim 19, wherein:
a mediolateral axis defining the longest line segment within said peripheral wall that is also perpendicular to said anteroposterior axis,
said first radius center disposed between said mediolateral axis and said anterior edge, said second radius center disposed posterior of said mediolateral axis.

37. The tibial prosthesis of claim 19, wherein:
said medial periphery defines a medial posterior edge generally opposite said anterior edge, a medial anteroposterior extent extending from said anterior edge to said medial posterior edge, and
said lateral periphery defines a lateral posterior edge generally opposite said anterior edge, a lateral anteroposterior extent extending from said anterior edge to said lateral posterior edge,
said medial anteroposterior extent larger than said lateral anteroposterior extent.

38. The tibial prosthesis of claim 19, wherein said anterior edge is substantially planar.

39. A tibial prosthesis comprising an asymmetric prosthesis periphery, said periphery comprising:
an anteroposterior axis dividing said prosthesis periphery into a medial compartment and a lateral compartment;
an anterior edge disposed between said medial compartment and said lateral compartment;
a lateral posterior edge generally opposite said anterior edge and forming a posterior boundary of said lateral compartment;
a medial posterior edge generally opposite said anterior edge and forming a posterior boundary of said medial compartment;
a lateral periphery extending from said anterior edge to said lateral posterior edge, said lateral periphery defining:
an anterior-lateral arc having an anterior-lateral arc center; and
a lateral arc having a lateral arc center, said lateral arc defining a tangent parallel to said anteroposterior axis;
a medial periphery extending from said anterior edge to said medial posterior edge, said medial periphery defining:
an anterior-medial arc having an anterior-medial arc center; and
a medial arc having a medial arc center, said medial arc defining a tangent parallel to said anteroposterior axis, a mediolateral axis defining the longest line segment within said prosthesis periphery that is also perpendicular to said anteroposterior axis,
said anterior-lateral arc center disposed between said mediolateral axis and said anterior edge,
said anterior-medial arc center disposed posterior of said mediolateral axis,
wherein said tibial prosthesis in combination with a tibial bearing component mountable to said tibial prosthesis, said anterior-lateral arc defining an anterior-lateral arc radius, said anterior-medial arc defining an anterior-medial arc radius,
said tibial bearing component comprising:
a lateral portion defining an anterior-lateral bearing corner defining a third radius having a third radial center, said third radial center substantially coincident with said anterior-lateral arc center in a transverse plane when said tibial bearing component is mounted to said tibial prosthesis, said third radius smaller than said anterior-lateral arc radius; and
a medial portion defining an anterior-medial bearing corner defining a fourth radius having a fourth radial center, said fourth radial center substantially coincident with said anterior-medial arc center in the transverse plane when said tibial bearing component is mounted to said tibial prosthesis, said fourth radius smaller than said anterior-medial arc radius, said fourth radius substantially larger than said third radius.

40. The tibial prosthesis of claim 39, wherein:
said lateral arc defines a lateral arc radius,
said lateral arc radius larger than said anterior-lateral arc radius by at least 42%.

41. The tibial prosthesis of claim 40, wherein said lateral arc radius is larger than said anterior-lateral arc radius by up to 142%.

42. The tibial prosthesis of claim 39, wherein said lateral arc defines a lateral arc radius, said lateral periphery comprising:
a posterior-lateral arc traversing an angular sweep between said lateral posterior edge and said lateral arc,
said posterior-lateral arc defining a posterior-lateral arc radius,
said lateral arc radius larger than said posterior-lateral arc radius by at least 198%.

43. The tibial prosthesis of claim 42, wherein said lateral arc radius is larger than said posterior-lateral arc radius by up to 324%.

44. The tibial prosthesis of claim 39, wherein:
said medial arc defines a medial arc radius,
said medial arc radius larger than said anterior-medial arc radius by up to 74%.

45. The tibial prosthesis of claim 39, wherein said medial arc defines a medial arc radius, said medial periphery comprising:
a posterior-medial arc traversing an angular sweep between said medial posterior edge and said medial arc,
said posterior-medial arc defining a posterior-medial arc radius,
said medial arc radius larger than said posterior-medial arc radius by up to 61%.

46. The tibial prosthesis of claim 39, wherein said anterior-lateral arc and said lateral arc each define respective lateral radii values that are different from one another.

47. The tibial prosthesis of claim 39, wherein at least one of said anterior edge, said lateral posterior edge and said medial posterior edge is planar.

48. The tibial prosthesis of claim 39, wherein said lateral periphery defines an arcuate anterior section between said anterior edge and said anterior-lateral arc.

49. The tibial prosthesis of claim 39, wherein:
said lateral periphery defines a plurality of adjacent lateral arcs including said anterior-lateral arc and said lateral arc, and
said medial periphery defines a plurality of adjacent medial arcs including said anterior-medial arc and said medial arc,
said plurality of adjacent lateral arcs greater in number as compared to said plurality of adjacent medial arcs.

50. The tibial prosthesis of claim 49, wherein said plurality of adjacent lateral arcs comprises at least five adjacent lateral arcs.

51. The tibial prosthesis of claim 49, wherein said plurality of adjacent medial arcs comprises up to three adjacent lateral arcs.

52. The tibial prosthesis of claim 39, wherein:
said anterior-lateral arc radius has a first angular sweep,
said anterior-medial arc radius has a second angular sweep similar to said first angular sweep,
said anterior-medial arc radius larger than said anterior-lateral arc radius.

53. The tibial prosthesis of claim 39, wherein said tibial prosthesis comprises a tibial baseplate having a proximal surface and an opposing distal surface, said distal surface comprising a bone contacting surface and said proximal surface comprising a tibial bearing engagement surface.

54. The tibial prosthesis of claim 53, wherein said tibial baseplate is sized and shaped to cover between about 60% and about 90% of a resected proximal surface of a tibia to create a buffer zone on all sides between a perimeter of a surface of the tibia and said prosthesis periphery.

55. The tibial prosthesis of claim 39, wherein:
said periphery defines a medial anteroposterior extent extending from said anterior edge to said medial posterior edge, and
said periphery defines a lateral anteroposterior extent extending from said anterior edge to said lateral posterior edge,
said medial anteroposterior extent larger than said lateral anteroposterior extent.

56. The tibial prosthesis of claim 39, wherein said anteroposterior axis is aligned with a home axis when said tibial prosthesis is mounted to a tibia, said home axis defined as a line extending from
a posterior point at a geometric center of an attachment area between a posterior cruciate ligament and the tibia, to
an anterior point disposed on an anterior tubercle of the tibia, the tubercle having a tubercle width W, said anterior point disposed on the tubercle at a location medially spaced from a midpoint of the tubercle by an amount equal to W/6.

57. The tibial prosthesis of claim 39, wherein:
said tibial prosthesis includes a PCL cutout area generally opposite said anterior edge and between said lateral periphery and said medial periphery, and
said anteroposterior axis bisects said anterior edge and bisects said PCL cutout area.

58. The tibial prosthesis of claim 39, wherein:
said medial periphery cooperates with said anteroposterior axis to bound a medial surface area,
said lateral periphery cooperates with said anteroposterior axis to bound a lateral surface area, and
said medial surface area is larger than said lateral surface area.

\* \* \* \* \*

UNITED STATES PATENT AND TRADEMARK OFFICE
CERTIFICATE OF CORRECTION

| | | |
|---|---|---|
| PATENT NO. | : 8,613,775 B2 | Page 1 of 1 |
| APPLICATION NO. | : 13/189336 | |
| DATED | : December 24, 2013 | |
| INVENTOR(S) | : Wentorf et al. | |

It is certified that error appears in the above-identified patent and that said Letters Patent is hereby corrected as shown below:

On the Title Page, Item (56)

On page 4, in column 1, under "Other Publications", line 2, delete "University.," and insert --University,--, therefor On page 4, in column 2, under "Other Publications", line 1, delete "S," and insert --S.,--, therefor In the Claims In column 25, line 32, in claim 1, delete "comer" and insert --corner--, therefor In column 29, line 2, in claim 33, after "to", insert --¶--, therefor In column 29, line 3, in claim 33, after "on", delete "¶", therefor Signed and Sealed this
Thirty-first Day of March, 2015

Michelle K. Lee
*Director of the United States Patent and Trademark Office*